US009974886B2

(12) United States Patent
Wang et al.

(10) Patent No.: US 9,974,886 B2
(45) Date of Patent: *May 22, 2018

(54) METHODS OF MANUFACTURING HYDROGEL MICROPARTICLES HAVING LIVING CELLS, AND COMPOSITIONS FOR MANUFACTURING A SCAFFOLD FOR TISSUE ENGINEERING

(71) Applicant: Nanyang Technological University, Singapore (SG)

(72) Inventors: Dongan Wang, Singapore (SG); Ting Ting Lau, Singapore (SG); Wenyan Leong, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/420,278

(22) PCT Filed: Jul. 26, 2013

(86) PCT No.: PCT/SG2013/000312
§ 371 (c)(1),
(2) Date: Feb. 6, 2015

(87) PCT Pub. No.: WO2014/025312
PCT Pub. Date: Feb. 13, 2014

(65) Prior Publication Data
US 2015/0217024 A1 Aug. 6, 2015

Related U.S. Application Data

(60) Provisional application No. 61/680,854, filed on Aug. 8, 2012.

(51) Int. Cl.
| | | |
|---|---|---|
| A61L 27/52 | (2006.01) | |
| A61L 27/38 | (2006.01) | |
| A61L 27/14 | (2006.01) | |
| A61L 27/22 | (2006.01) | |
| A61L 27/56 | (2006.01) | |

(52) U.S. Cl.
CPC .............. *A61L 27/52* (2013.01); *A61L 27/14* (2013.01); *A61L 27/222* (2013.01); *A61L 27/38* (2013.01); *A61L 27/3817* (2013.01); *A61L 27/56* (2013.01); *A61L 2400/06* (2013.01); *A61L 2400/08* (2013.01); *A61L 2430/00* (2013.01); *A61L 2430/06* (2013.01)

(58) Field of Classification Search
CPC ........ A61L 27/14; A61L 27/222; A61L 27/38; A61L 27/3817; A61L 27/56; A61L 2400/06; A61L 2400/08; A61L 2430/06; A61L 27/52; A61L 2430/00
See application file for complete search history.

(56) References Cited

U.S. PATENT DOCUMENTS

| | | | | |
|---|---|---|---|---|
| 4,798,786 | A | * 1/1989 | Tice | ..................... A61K 9/5052 435/177 |
| 2002/0052044 | A1 | * 5/2002 | Jeschke | ................... A61L 27/20 435/325 |
| 2011/0104052 | A1 | 5/2011 | Barnett et al. | |

FOREIGN PATENT DOCUMENTS

WO 2010/132028 11/2010

OTHER PUBLICATIONS

Ahmadi et al., "Enhanced attachment, growth and migration of smooth muscle cells on microcarriers produced using thermally induced phase separation," *Acta Biomaterialia* 7:1542-1549, 2011.
Benjamin et al., "Cytoskeleton of Cartilage Cells," *Microscopy Research and Technique* 28:372-377, 1994.
Chen et al., "PHBV microspheres as neural tissue engineering scaffold support neuronal cell growth and axon-dendrite polarization," *Acta Biomaterialia* 8:540-548, 2012.
Chia et al., "TGF-β1 Regulation in Hepatocyte-NIH3T3 Co-Culture Is Important for the Enhanced Hepatocyte Function in 3D Microenvironment," *Biotechnology and Bioengineering* 89(5):565-573, 2005.
Choi et al., "Biodegradable porous beads and their potential applications in regenerative medicine," *Journal of Materials Chemistry* 22:11442-11451, 2012.
Coward et al., "Alginate-encapsulated HepG2 Cells in a Fluidized Bed Bioreactor Maintain Function in Human Liver Failure Plasma," *Artificial Organs* 33(12):1117-1126, 2009.
Efrat et al., "Making β cells from adult tissues," *Trends in Endocrinology and Metabolism* 23(6):278-285, 2012.
Franco et al., "Development and optimization of a dual-photoinitiator, emulsion-based technique for rapid generation of cell-laden hydrogel microspheres," *Acta Biomaterialia* 7:3267-3276, 2011.
Freed et al., "Neocartilage formation in vitro and in vivo using cells cultured on synthetic biodegradable polymers," *Journal of Biomedical Materials Research* 27:11-23, 1993.
Freed et al., "Chondrogenesis in a Cell-Polymer-Bioreactor System," *Experimental Cell Research* 240:58-65, 1998.
Gong et al., "An improved injectable polysaccharide hydrogel: modified gellan gum for long-term cartilage regeneration in vitro," *Journal of Materials Chemistry* 19:1968-1977, 2009.

(Continued)

*Primary Examiner* — Satyendra K Singh
(74) *Attorney, Agent, or Firm* — Seed IP Law Group LLP

(57) ABSTRACT

Method of manufacturing hydrogel microparticles comprising one or more species of living cells attached thereon and/or encapsulated therein is provided. The method includes dissolving a hydrogel-forming agent in an aqueous medium to form a solution; suspending one or more species of living cells in the solution to form a cell suspension; dispersing the cell suspension into an organic oil to form a microemulsion; and subjecting the microemulsion to conditions that allow the hydrogel-forming agent to form hydrogel microparticles comprising one or more species of living cells attached thereon and/or encapsulated therein. Composition comprising a mixture of a degradable hydrogel and at least one hydrogel microparticle having one or more species of living cells, and method of manufacturing a scaffold for tissue engineering are also provided.

13 Claims, 14 Drawing Sheets

(56) References Cited

OTHER PUBLICATIONS

Gong et al., "Microcavitary Hydrogel-Mediating Phase Transfer Cell Culture for Cartilage Tissue Engineering," *Tissue Engineering: Part A 16*(12):3611-3622, 2010.
Goto et al., "Hepatocyte Transplantation Through the Hepatic Vein: A New Route of Cell Transplantation to the Liver," *Cell Transplantation 20*:1259-1270, 2011.
Huang et al., "Mesenchymal stem cells delivered in a microsphere-based engineered skin contribute to cutaneous wound healing and sweat gland repair," *Journal of Dermatological Science 66*:29-36, 2012.
Hughes et al., "Current Status of Hepatocyte Transplantation," *Transplantation 93*:342-347, 2012.
Hwang et al., "Fabrication of three-dimensional porous cell-laden hydrogel for tissue engineering," *Biofabrication 2*:035003, 2010. (12 pages).
Ijima et al., "Hepatocyte growth factor and epidermal growth factor promote spheroid formation in polyurethane foam/hepatocyte culture and improve expression and maintenance of albumin production," *Biochemical Engineering Journal 47*:19-26, 2009.
Inamori et al., "An Approach for Formation of Vascularized Liver Tissue by Endothelial Cell-Covered Hepatocyte Spheroid Integration," *Tissue Engineering: Part A 15*(8):2029-2037, 2009.
Itskovitz-Eldor et al., "Differentiation of Human Embryonic Stem Cells into Embryoid Bodies Comprising the Three Embryonic Germ Layers," *Molecular Medicine 6*(2):88-95, 2000.
Jefferies et al., "Differences in metabolic parameters and gene expression related to Osteochondrosis/Osteoarthrosis in pigs fed 25-hydroxyvitamin $D_3$," *Vet. Res. 33*:383-396, 2002.
Kim et al., "Preserved liver-specific functions of hepatocytes in 3D co-cultured with endothelial cell sheets," *Biomaterials 33*:1406-1413, 2012.
Kojima et al., "Spheroid array of fetal mouse liver cells constructed on a PEG-gel micropatterned surface: upregulation of hepatic functions by co-culture with nonparenchymal liver cells," *Lab Chip 9*:1991-1993, 2009.
Lakey et al., "Technical aspects of islet preparation and transplantation," *Transpl Int 16*:613-632, 2003.
Lau et al., "Cell delivery with genipin crosslinked gelatin microspheres in hydrogel/microcarrier composite," *Composites Science and Technology 70*:1909-1914, 2010.
Lau et al., "Genipin-crosslinked microcarriers mediating hepatocellular aggregates formation and functionalities," *J Biomed Mater Res Part A 96A*:204-211, 2011.
Lee et al., "Diffusion-mediated in situ alginate encapsulation of cell spheroids using microscale concave well and nanoporous membrane," *Lab Chip 11*:1168-1173, 2011.
Li et al., "Regulation of Cytochrome P450 Enzymes by Aryl Hydrocarbon Receptor in Human Cells—CYP1A2 Expression in the LS180 Colon Carcinoma Cell Line After Treatment with 2,3,7,8-Tetrachlorodibenzo-ρ-Dioxin or 3-Methylcholanthrene," *Biochemical Pharmacology 56*:599-612, 1998.
Liang et al., "Dual delivery for stem cell differentiation using dexamethasone and bFGF in/on polymeric microspheres as a cell carrier for nucleus pulposus regeneration," *J. Mater. Sci: Mater Med 23*:1097-1107, 2012.
Lu et al., "Three-dimensional co-culture of rat hepatocyte spheroids and NIH/2T2 fibroblasts enhances hepatocyte functional maintenance," *Acta Biomaterialia 1*:399-410, 2005.
Mavri-Damelin et al., "Ornithine transcarbamylase and arginase I deficiency are responsible for diminished urea cycle function in the human hepatoblastoma cell line HepG2," *The International Journal of Biochemistry & Cell Biology 39*:555-564, 2007.
Mori et al., "Micropatterned Organoid Culture of Rat Hepatocytes and HepG2 Cells," *Journal of Bioscience and Bioengineering 106*(3):237-242, 2008.
Nakazawa et al., "Hepatocyte spheroid culture on a polydimethylsiloxane chip having microcavities," *J. Biomater. Sci. Polymer Edn. 17*(8):859-873, 2006.

Ng et al., "Biomechanical study of the edge outgrowth phenomenon of encapsulated chondrocytic isogenous groups in the surface layer of hydrogel scaffolds for cartilage tissue engineering," *Acta Biomaterialia 8*:244-252, 2012.
Nibourg et al., "Stable Overexpression of *Pregnane X Receptor* in HepG2 Cells Increases Its Potential for Bioartificial Liver Application," *Liver Transplantation 16*:1075-1085, 2010.
Nicodemus et al., "Cell Encapsulation in Biodegradable Hydrogels for Tissue Engineering Applications," *Tissue Engineering: Part B 14*(2):149-165, 2008.
Ravichandran et al., "Advances in Polymeric Systems for Tissue Engineering and Biomedical Applications," *Macromolecular Bioscience 12*:286-311, 2012.
Reis et al., "Review and current status of emulsion/dispersion technology using an internal gelation process for the design of alginate particles," *Journal of Microencapsulation 23*(3):245-257, 2006.
Rountree et al., "Stem Cells in Liver Diseases and Cancer: Recent Advances on the Path to New Therapies," *Hepatology 55*:298-306, 2012.
Schrobback et al., "Adult Human Articular Chondrocytes in a Microcarrier-Based Culture System: Expansion and Redifferentiation," *J. Orthop Res 29*:539-546, 2011.
Sheridan et al., "Analysis of Embryoid Bodies Derived from Human Induced Pluripotent Stem Cells as a Means to Assess Pluripotency," *Stem Cells International*: 2012. (10 pages).
Sommar et al., "Engineering three-dimensional cartilage- and bone-like tissues using human dermal fibroblasts and macroporous gelatine microcarriers," *Journal of Plastic, Reconstructive & Aesthetic Surgery 63*:1036-1046, 2010.
Su et al., "Creating a Living Hyaline Cartilage Graft Free from Non-Cartilaginous Constituents: An Intermediate Role of a Biomaterial Scaffold," *Adv. Funct. Mater. 22*:972-978, 2012.
Swamy et al., "Preparation of Sodium Alginate/Poly(vinyl alcohol) Blend Microspheres for Controlled Release Applications," *J. Appl. Polym. Sci. 125*:555-561, 2012.
Thomas et al., "The Effect of Three-Dimensional Co-Culture of Hepatocytes and Hepatic Stellate Cells on Key Hepatocyte Functions in vitro," *Cells Tissues Organs 181*:67-79, 2005.
Tong et al., "Long-Term Culture of Adult Rat Hepatocyte Spheroids," *Experimental Cell Research 200*:326-332, 1992.
Tostões et al., "Perfusion of 3D Encapsulated Hepatocytes—A Synergistic Effect Enhancing Long-Term Functionality in Bioreactors," *Biotechnol. Bioeng. 108*:41-49, 2011.
Turner et al., "Human Hepatoblast Phenotype Maintained by Hyaluronan Hydrogels," *J. Biomed. Mater Res Part B: Appl Biomater 82B*:156-168, 2007.
Verma et al., "Formation and characterization of three dimensional human hepatocyte cell line spheroids on chitosan matrix for in vitro tissue engineering applications," *In Vitro Cell. Dev. Biol.—Animal 43*:328-337, 2007.
Wang et al., "A novel gellan gel-based microcarrier for anchorage-dependent cell delivery," *Acta Biomaterialia 4*:1226-1234, 2008.
Wang et al., "Silk nanospheres and microspheres from silk/pva blend films for drug delivery," *Biomaterials 31*:1025-1035, 2010.
Wynn et al., "A small proportion of mesenchymal stem cells strongly expresses functionally active CXCR4 receptor capable of promoting migration to bone marrow," *Blood 104*:2643-2645, 2004.
Xiong et al., "Isolation of Human Fetal Liver Progenitors and Their Enhanced Proliferation by Three-Dimensional Coculture with Endothelial Cells," *Tissue Engineering: Part A 14*(6):995-1006, 2008.
Yamazaki et al., "Neurotrophic Effects of Genipin on Neuro2a Cells," *Journal of Health Science 51*(6):687-692, 2005.
Yang et al., "Development of highly porous large PLGA microparticles for pulmonary drug delivery," *Biomaterials 30*:1947-1953, 2009.
Yao et al., "Alginate and alginate/gelatin microspheres for human adipose-derived stem cell encapsulation and differentiation," *Biofabrication 4*:025007, 2012. (11 pages).

(56) References Cited

OTHER PUBLICATIONS

Yoshida et al., "Use of human hepatocyte-like cells derived from induced pluripotent stem cells as a model for hepatocytes in hepatitis C virus infection," *Biochemical and Biophysical Research Communications 416*:119-124, 2011.

Yoshimoto et al., "Inverted pattern formation of cell microarrays on poly(ethylene glycol) (PEG) gel patterned surface and construction of hepatocyte spheroids on unmodied PEG gel microdomains," *Lab Chip 9*: 1286-1289, 2009.

Young et al., "Combining Submerged Electrospray and UV Photopolymerization for Production of Synthetic Hydrogel Microspheres for Cell Encapsulation," *Biotechnol. Bioeng. 109*:1561-1570, 2012.

Yu et al., "Cell Therapies for Liver Diseases," *Liver Transplantation 18*:9-21, 2012.

Zhang et al., "Alginate microsphere filled with carbon nanotube as drug carrier," *International Journal of Biological Macromolecules 47*:389-395, 2010.

Zhou et al., "Expansion and Delivery of Adipose-Derived Mesenchymal Stem Cells on Three Microcarriers for Soft Tissue Regeneration," *Tissue Engineering: Part A 17*(23 and 24):2981-2997, 2011.

\* cited by examiner (A)

(B)

(C)

(D)

(E)

(F)

(C)

(D)

(A)

(B)

METHODS OF MANUFACTURING HYDROGEL MICROPARTICLES HAVING LIVING CELLS, AND COMPOSITIONS FOR MANUFACTURING A SCAFFOLD FOR TISSUE ENGINEERING

CROSS-REFERENCE TO RELATED APPLICATION

This application claims the benefit of priority of U.S. provisional application No. 61/680,854 filed on 8 Aug. 2012, the content of which is incorporated herein by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_475USPC_SEQUENCE_LISTING.txt. The text file is 5.1 KB, was created on Feb. 5, 2015, and is being submitted electronically via EFS-Web.

TECHNICAL FIELD

The invention refers to the field of hydrogel microparticles, and use of hydrogel microparticles in forming scaffolds in tissue engineering usable to replace tissues, such as an organ, bone or parts of it.

BACKGROUND

Microspheres have been used as delivery vehicles for drugs and cells, as they provide a minimally invasive means of transplantation. In particular, many materials and fabrication methods in the delivery of cells for regenerative medicine purposes have been explored because of their advantages: simplicity of large-scale culture of cells in microspheres of controlled sizes, provision of a tunable three-dimensional (3-D) environment for cells, ability to incorporate biochemical signals and biomechanical moieties, as well as simplicity of direct injection of cell-loaded microspheres into defect sites without trypsinization.

Studies were usually done through a two-step method of first fabricating microspheres, for example, through single or double emulsion methods, electrospraying and thermally induced phase separation, and subsequently seeding cells onto them. Although the above-mentioned methods were able to support cells, the microsphere fabrication techniques usually required specialized equipment or a significant amount of time, as thorough washing steps were necessary after chemical-based treatment.

Furthermore, these techniques largely catered for anchorage dependent cells such as fibroblasts. Several other groups reported techniques of direct cell encapsulation into microspheres using either synthetic polyethylene glycol diacrylate, which requires surface modification and addition of enzyme-degradation sites, or natural biopolymers such as alginate, which possess batch-to-batch variation as well as uncontrollable degradation rates.

Tissue engineering techniques generally require the use of a temporary scaffold as a three-dimensional template for initial cell attachment and subsequent tissue formation. The ability of the scaffold to be metabolised by the body allows it to be gradually replaced by new cells to form functional tissue. As such, scaffold design is one of the most important aspects of tissue engineering.

Hydrogels have shown great promise as a scaffold for tissue engineering due to their tissue-like water content, good biocompatibility, and injectable accessibility for in situ grafting. However, substantial challenges remain in the use of hydrogels as scaffold and cell delivery materials. For example, hydrogels have low cell affinity. Therefore, when they are used to encapsulate cells commonly used in regenerative medicine, such as fibroblasts, osteoblasts, endothelial, epithelial and smooth muscle cells, these anchorage dependent cells (ADC) do not spread out in the hydrogel framework but are constrained into a spheroidal shape, thereby leading to poor settlement and frequent occurrence of cell death. In addition, spatial confinement of cells within hydrogel bulk prevents cell migration and cell-cell interaction which are essential in mediating cell differentiation and tissue regeneration, as well as inhibiting cell aggregation which is particularly necessary for the reorganization of tissues, such as cartilage and liver.

The liver is the largest internal organ in human body, responsible for a number of essential functions such as detoxification and protein synthesis. Alcoholism and diseases such as hepatitis account for most acute or chronic liver failures. Currently, tens of millions of people worldwide are suffering from this ailment, but only a small percentage of them receive liver transplants because of a severe shortage of liver donors. Additionally, patients receiving successful liver transplantation do not always have a full recovery. They risk immune-rejections and have life-long dependence on immunosuppressive drugs. The rising prevalence of liver diseases has prompted researchers to search for alternative treatments, such as liver cell transplantation, as possible solutions; these have been extensively explored in the past decade.

Liver cell transplantation relies on the introduction of mature hepatocytes or liver stem cells into the host to restore, maintain or improve defective liver functions. Mature hepatocytes have suboptimal proliferation capacity in vitro and they rapidly lose their phenotype in two-dimensional monolayer cultures. Although hepatocyte transplantation may have an immediate therapeutic effect, its clinical application is limited by the availability and quality of the cells. Studies have reported the maintenance of liver-specific functionalities in three-dimensional culture, when hepatocellular aggregates or spheroids were formed. In this sense, generating liver cell spheroids with controllable size and shape poses one of the key challenges in liver tissue engineering research and development.

Various methodologies have been explored to aid the formation of these spheroids. Common approaches include using bioreactors, photolithography or micropatterning to create molds of appropriate sizes. Nonetheless, these approaches require specialized equipment in order to generate spheroids of controllable size and have faced considerable difficulties in scaling-up.

In view of the above, there remains a need for methods of forming hydrogel microparticles, which may be used in compositions for the manufacture of scaffolds for tissue engineering, which addresses one or more of the above-mentioned issues.

SUMMARY

In a first aspect, the invention refers to a method of manufacturing hydrogel microparticles comprising one or more species of living cells attached thereon and/or encapsulated therein. The method comprises
a) dissolving a hydrogel-forming agent in an aqueous medium to form a solution;
b) suspending one or more species of living cells in the solution to form a cell suspension;
c) dispersing the cell suspension into an organic oil to form a microemulsion; and
d) subjecting the microemulsion to conditions that allow the hydrogel-forming agent to form hydrogel microparticles comprising one or more species of living cells attached thereon and/or encapsulated therein.

In a second aspect, the invention refers to a composition comprising a mixture of a degradable hydrogel and at least one hydrogel microparticle comprising one or more species of living cells attached thereon and/or encapsulated therein according to the first aspect.

In a third aspect, the invention refers to a composition comprising a mixture of a degradable hydrogel and at least one hydrogel microparticle comprising one or more species of living cells attached thereon and/or encapsulated therein, wherein at least one of the degradable hydrogel and the hydrogel microparticle comprises a porogen agent that effects degradation of the hydrogel microparticle.

In a fourth aspect, the invention refers to a method of manufacturing a scaffold for tissue engineering. The method comprises
a) providing a composition comprising a mixture of a degradable hydrogel and at least one hydrogel microparticle comprising one or more species of living cells attached thereon and/or encapsulated therein;
b) incubating the composition under conditions which allow proliferation of the one or more species of living cells and degradation of the at least one hydrogel microparticle in the degradable hydrogel to allow the one or more species of living cells to proliferate and to allow the at least one hydrogel microparticle to degrade; and
c) degrading the degradable hydrogel of the incubated mixture to obtain a scaffold.

BRIEF DESCRIPTION OF THE DRAWINGS

The invention will be better understood with reference to the detailed description when considered in conjunction with the non-limiting examples and the accompanying drawings, in which.

* represents p<0.05 when compared to control sample of that day. Y-axis: absorbance; x-axis: time (day).

Figure 11:
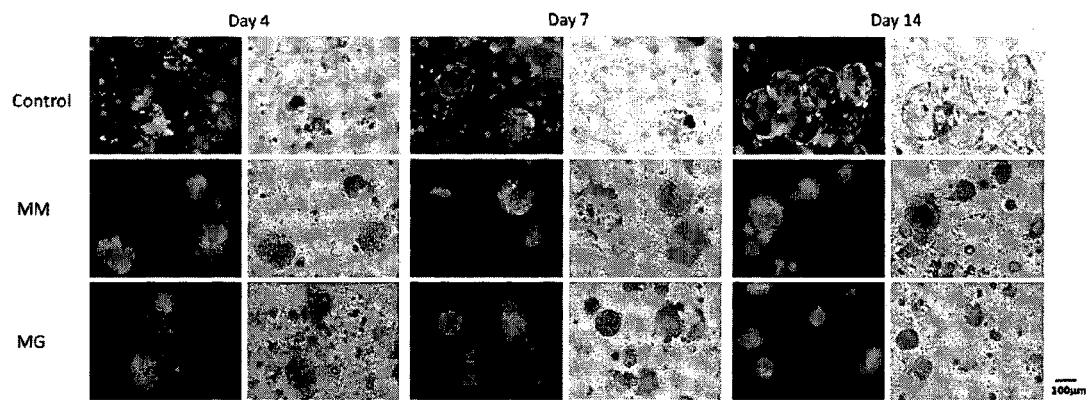

FIG. 11 shows live/dead staining and phase contrast images of the cells in control, MM and MG constructs on day 4, 7 and 14. Scale bar denotes a length of 100 μm.

Figure 12:
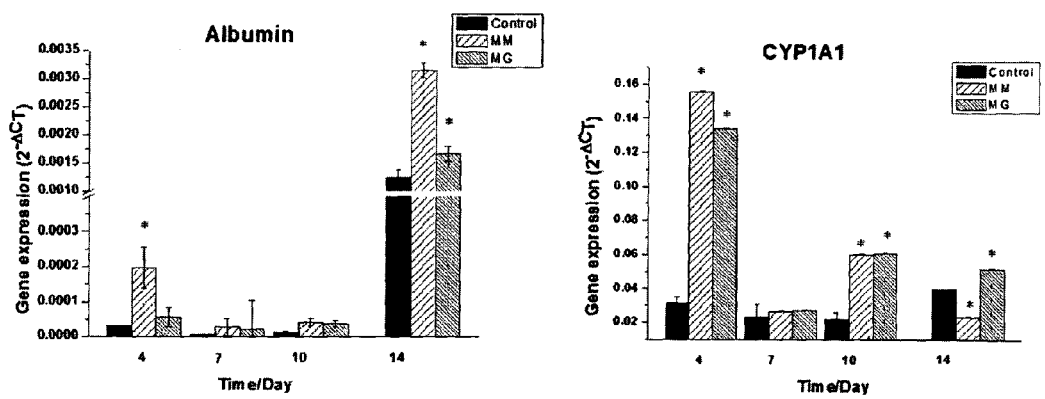

FIG. 12 shows gene expression of albumin and cytochrome P4501A1 (CYP1A1) of control, MM and MG constructs at various time points. * represents p<0.05 when compared to control sample of that day. Y-axis: gene-expression ($2^{-\Delta C_T}$); x-axis: time (day).

Figure 13:
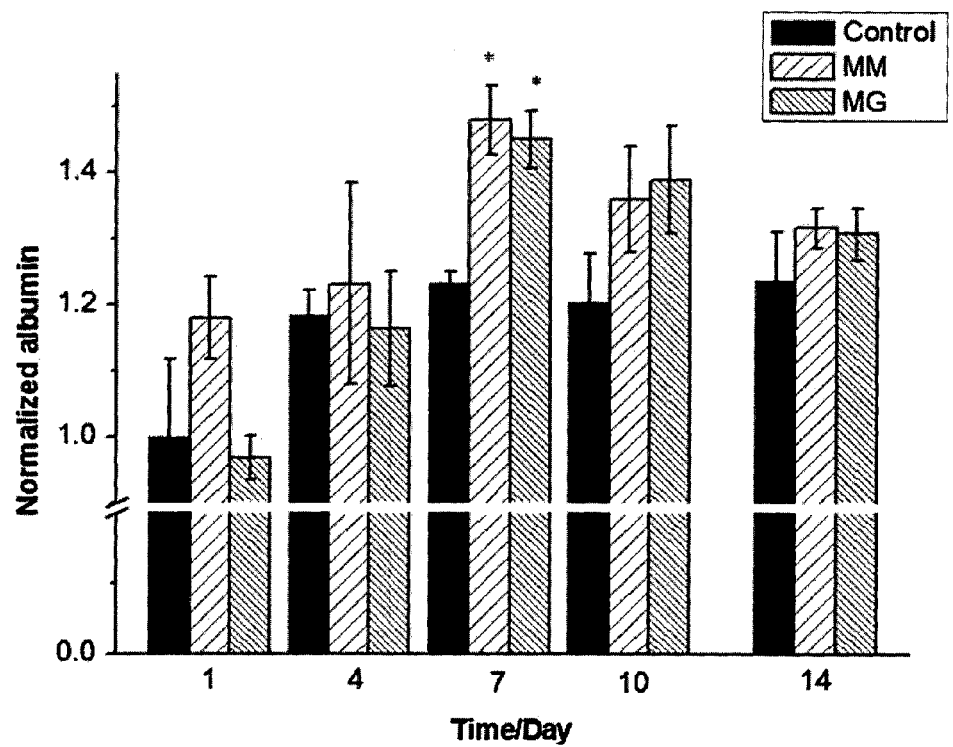

FIG. 13 is a graph showing albumin secretion from control, MM and MG constructs at various time points. * represents p<0.05 when compared to control sample of that day. Y-axis: normalized albumin; x-axis: time (day).

Figure 14:
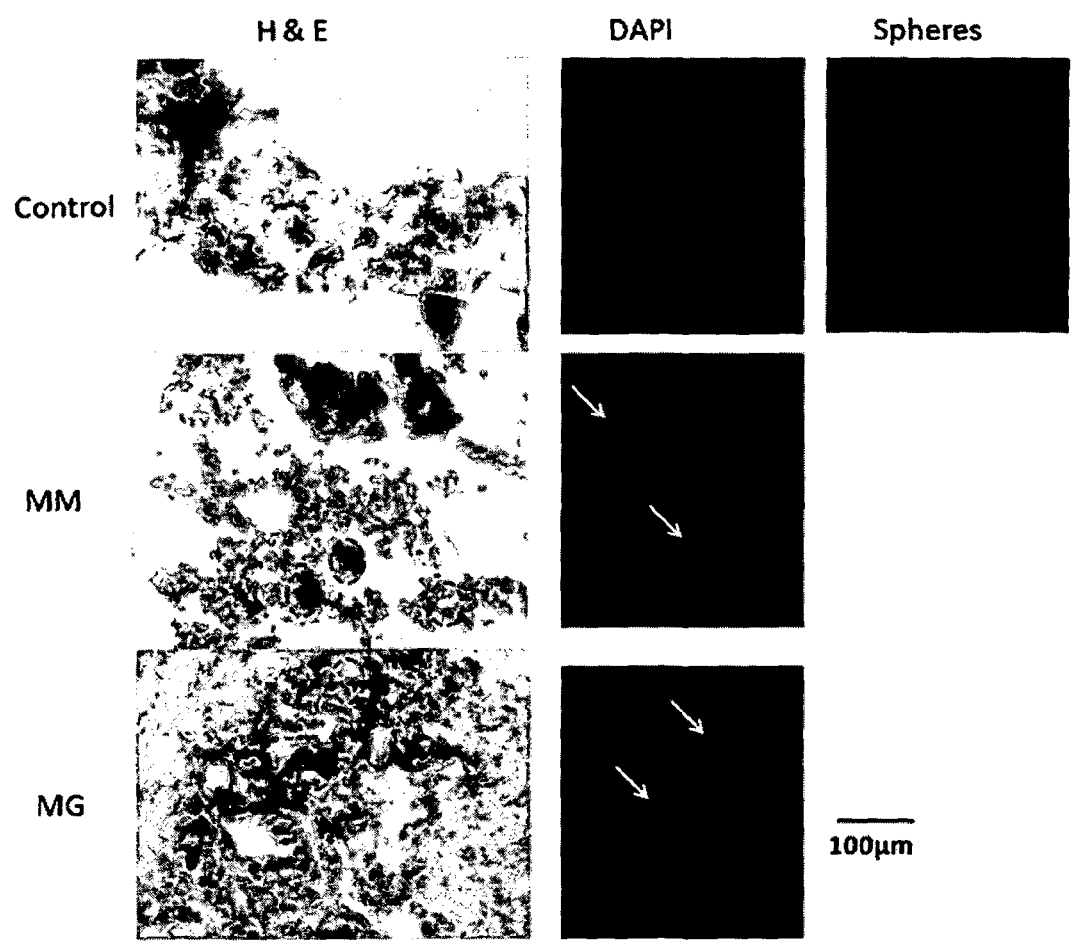

FIG. 14 shows histochemical staining of control, MM and MG constructs 14 days after subcutaneous implantation in nude mice. Red dotted lines outline the cavities while arrows indicate HepG2 cell aggregates within the constructs. Scale bar denotes a length of 100 μm.

Figure 15:
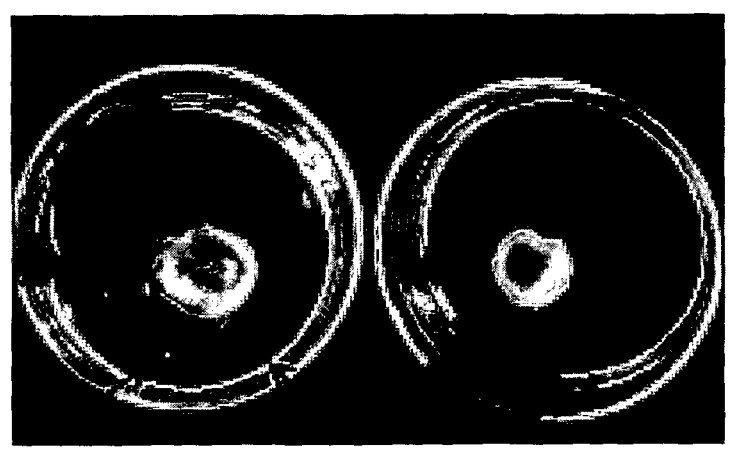

FIG. 15 shows a photograph of constructs after treatment with sodium citrate solution at Day 21. Left: LhCG-blkMC and right: LhCG-tDGMC. Integrity of LhCG-tDGMC construct was retained, but visibly less so for the LhCG-blkMC construct which partially collapsed. Red arrows indicate pieces of debris.

DETAILED DESCRIPTION

In a first aspect, the present invention refers to a method of manufacturing hydrogel microparticles comprising one or more species of living cells attached thereon and/or encapsulated therein.

Advantageously, the method of manufacturing hydrogel microparticles allows loading of cells in hydrogel microparticles with high cell viability. The hydrogel microparticles having one or more species of living cells attached thereon and/or encapsulated therein may be formed from a degradable hydrogel, and may be dispersed in a degradable hydrogel matrix, such that by preferentially degrading the hydrogel microparticles with respect to the hydrogel matrix using methods such as applying heat or a porogen agent, the cells contained in the hydrogel microparticles may be released and suspended inside the cavities. Accordingly, the hydrogel microparticles may perform a dual role as a cell delivery vehicle and as a porogen for creation of cavities in the hydrogel matrix. This provides the living cells with an improved permeable environment and space for cell proliferation, which translates into high cell viability such as that demonstrated herein.

As used in this application, the term "hydrogel" refers to a broad class of polymeric materials, that may be natural or synthetic, which have an affinity for an aqueous medium, and may absorb large amounts of the aqueous medium, but which do not normally dissolve in the aqueous medium.

Generally, a hydrogel may be formed by using at least one, or one or more types of hydrogel-forming agent, and setting or solidifying the one or more types of hydrogel-forming agent in an aqueous medium to form a three-dimensional network, wherein formation of the three-dimensional network may cause the one or more types of hydrogel-forming agent to gel so as to form the hydrogel. The term "hydrogel-forming agent", also termed herein as "hydrogel precursor", refers to any chemical compound that may be used to make a hydrogel. The hydrogel-forming agent may comprise a physically cross-linkable polymer, a chemically cross-linkable polymer, or mixtures thereof.

Physically cross-linking may take place via, for example, complexation, hydrogen bonding, desolvation, van der Waals interactions, or ionic bonding. In various embodiments, a hydrogel may be formed by self-assembly of one or more types of hydrogel-forming agents in an aqueous medium. The term "self-assembly" refers to a process of spontaneous organization of components of a higher order structure by reliance on the attraction of the components for each other, and without chemical bond formation between the components. For example, polymer chains may interact with each other via any one of hydrophobic forces, hydrogen bonding, Van der Waals interaction, electrostatic forces, or polymer chain entanglement, induced on the polymer chains, such that the polymer chains aggregate or coagulate in an aqueous medium to form a three-dimensional network, thereby entrapping molecules of water to form a hydrogel. Examples of physically cross-linkable polymer that may be used include, but are not limited to, gelatin, alginate, pectin, furcellaran, carageenan, chitosan, derivatives thereof, copolymers thereof, and mixtures thereof.

Chemical crosslinking may take place via, for example, chain reaction (addition) polymerization, and step reaction (condensation) polymerization. The term "chemical cross-link" as used herein refers to an interconnection between polymer chains via chemical bonding, such as, but not limited to, covalent bonding, ionic bonding, or affinity interactions (e.g. ligand/receptor interactions, antibody/antigen interactions, etc.). Examples of chemically cross-linkable polymer that may be used include, but are not limited to, starch, gellan gum, dextran, hyaluronic acid, poly(ethylene oxides), polyphosphazenes, derivatives thereof, copolymers thereof, and mixtures thereof. Such polymers may be functionalized with a methacrylate group for example, and may be cross-linked in situ via polymerization of these groups during formation of the emulsion droplets in the fabrication process.

Chemical cross-linking may take place in the presence of a chemical cross-linking agent. The term "chemical cross-linking agent" refers to an agent which induces chemical cross-linking. The chemical cross-linking agent may be any agent that is capable of inducing a chemical bond between adjacent polymeric chains. For example, the chemical cross-linking agent may be a chemical compound. Examples of chemical compounds that may act as cross-linking agent include, but are not limited to, 1-ethyl-3-[3-dimethylaminopropyl]carbodiimide hydrochloride (EDC), vinylamine, 2-aminoethyl methacrylate, 3-aminopropyl methacrylamide, ethylene diamine, ethylene glycol dimethacrylate, methymethacrylate, N,N'-methylene-bisacrylamide, N,N'-methylene-bis-methacrylamide, diallyltartardiamide, allyl (meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate, diallyl phthalate, transglutaminase, derivatives thereof or mixtures thereof.

In some embodiments, the hydrogel-forming agents are themselves capable of chemical or physical cross-linking without using a cross-linking agent.

Besides the above-mentioned, the hydrogel-forming agents may be cross-linked using a cross-linking agent in the form of an electromagnetic wave. The cross-linking may be carried out using an electromagnetic wave, such as gamma or ultraviolet radiation, which may cause the polymeric chains to cross-link and form a three-dimensional matrix, thereby entrapping water molecules to form a hydrogel.

Therefore, choice of cross-linking agent is dependent on the type of polymeric chain and functional group present, and a person skilled in the art would be able to choose the appropriate type of cross-linking agent accordingly.

In various embodiments, the hydrogel-forming agent consists essentially of a physically cross-linkable polymer. In some embodiments, the hydrogel-forming agent comprises gelatin. In specific embodiments, the hydrogel-forming agent consists essentially of or consists of gelatin. The term "gelatin" as used herein refers to protein substances derived from collagen. In the context of the present invention, "gelatin" also refers to equivalent substances such as synthetic analogues of gelatin. Generally, gelatin may be classified as alkaline gelatin, acidic gelatin, or enzymatic gelatin. Alkaline gelatin may be obtained from the treatment of collagen with a base such as sodium hydroxide or calcium hydroxide. Acidic gelatin may be obtained from the treatment of collagen with an acid such as hydrochloric acid. Enzymatic gelatin may be obtained from the treatment of collagen with an enzyme such as hydrolase. As gelatin may be a form of hydrogel, factors that affect degradation behavior of hydrogels as mentioned herein may also apply to gelatin.

The method of the first aspect includes dissolving a hydrogel-forming agent in an aqueous medium to form a solution. The terms "aqueous medium" and "aqueous solution" as used herein are used interchangeably, and refers to water or a solution based primarily on water such as phosphate buffered saline (PBS), or water containing a salt dissolved therein. The aqueous medium may also comprise or consist of a cell culture medium. The term "cell culture medium" refers to any liquid medium which enables cells proliferation. Growth media are known in the art and can be selected depending of the type of cell to be grown. For example, a growth medium for use in growing mammalian cells is Dulbecco's Modified Eagle Medium (DMEM) which can be supplemented with heat inactivated fetal bovine serum.

The hydrogel-forming agent may be at least substantially or completely dissolved in the aqueous medium to form a solution. Agitation, for example, by stirring or sonication may be carried out to enhance the rate at which the hydrogel-forming agent dissolves in the aqueous medium. In some cases, heat energy may optionally be applied to the aqueous medium to increase the dissolve rate of the hydrogel-forming agent in the aqueous medium. For example, dissolving the hydrogel-forming agent in an aqueous medium may be carried out at a temperature in the range from about 20° C. to about 45° C., such as from about 20° C. to about 40° C., about 20° C. to about 35° C., about 20° C. to about 30° C., about 25° C. to about 45° C., about 30° C. to about 45° C., about 35° C. to about 45° C., about 30° C. to about 40° C., about 35° C. to about 40° C., about 30° C., 32° C., 34° C., 36° C., 38° C. or 40° C. In some embodiments, dissolving the hydrogel-forming agent in an aqueous medium is carried out at a temperature of about 37° C.

In various embodiments, dissolving the hydrogel-forming agent in the aqueous medium is carried out under sonication. Advantageously, by applying a heat treatment and/or sonication, the rate at which the hydrogel-forming agent is dissolved in the aqueous medium may be improved substantially.

Concentration of the hydrogel-forming agent in the solution may influence the size of hydrogel microparticles formed. Generally, a larger amount of the hydrogel-forming agent results in formation of a larger size hydrogel microparticle. In various embodiments, the amount of hydrogel-forming agent in the solution may be in the range from about 1% (w/v) to about 10% (w/v), such as about 1% (w/v) to about 8% (w/v), about 1% (w/v) to about 6% (w/v), about 1% (w/v) to about 5% (w/v), about 2% (w/v) to about 8% (w/v), about 2% (w/v) to about 6% (w/v), about 2% (w/v) to about 5% (w/v), about 3% (w/v) to about 8% (w/v), about 3% (w/v) to about 6% (w/v), about 3% (w/v) to about 5% (w/v), about 8% (w/v) to about 10% (w/v), about 6% (w/v) to about 10% (w/v), about 4% (w/v) to about 10% (w/v), about 4% (w/v) to about 8% (w/v), about 4% (w/v) to about 6% (w/v), about 4% (w/v), about 5% (w/v), or about 6% (w/v). For example, the amount of hydrogel-forming agent in the solution may be about 5% (w/v).

The method of the second aspect further comprises suspending one or more species of living cells in the solution to form a cell suspension. One or more species of living cells, such as one, two, three, four or five species of living cells are comprised in the cell suspension. The term "living cell" refers to any cell that is capable of cell division or contains a nucleus. A "living cell" also refers to a cell that has active metabolic machinery (e.g. mitochondria). The living cells may be eukaryotic cells, prokaryotic cells or archaea. As used herein, the term "eukaryotic cell" refers to any animal or plant cell having a definitive nucleus. Eukaryotic cells of animals include cells of vertebrates such as mammals, and cells of invertebrates such as insects. Examples of eukaryotic cells of plants include yeast cells, and algae cells. Eukaryotic cells may also comprise antibody producing cells, such as hybridoma. The term "prokaryotic cell" refers to a cell of a prokaryotic organism that lacks a definitive nucleus. Examples of prokaryotic cells may include, but are not limited to, the genus *Escherichia*, *Bacillus* or *Lactococcus*. Some examples of prokaryotic cell species from these genera are *Escherichia coli*, *Bacillus subtilis* or *Lactococcus lactis*. The term "archaea" refers to a group of single-celled microorganisms which has no cell nucleus or any other organelles within their cells.

The eukaryotic cell may be an anchorage dependent cell. An anchorage dependent cell refers to any cell which grows and multiplies when attached to a solid support material, and is not able to grow when present in a suspension. In some embodiments, the anchorage dependent cell may be a mammalian cell. A mammalian cell is any cell that is derived from a mammal. A mammalian cell may include a mammalian cell line. In one embodiment, the mammalian cell may be a human cell. Examples of a human cell include, but are not limited to, an osteogenic cell, a fibroblast, an epidermal cell, an adipocyte, a neural cell, an endothelial cell, an epithelial cell, a keratinocyte, a hepatocyte, a myocyte, a cell from joint ligament, a cell from the nucleus pulposis, a HEK 293 cell and PER.C6® cell. For such cells, conditions of attachment of the cells to a particular substrate greatly influence their subsequent function.

An osteogenic cell refers to an osteoblast or a progenitor osteoblast cell, which gives rise to a bone tissue. A fibroblast is a spindle shaped cell which may rapidly replicate and synthesize a fibrous matrix composed of a variety of extracellular matrix molecules including Type I Collagen, and which may be found in skin. An epidermal cell refers to a cell of the epidermis, wherein the epidermis is the outer layer of skin and is composed of four types of cells, i.e. keratinocyte, melanocyte, Langerhans cell, and Merkel cell. The term "adipocyte" refers to a cell existing in or derived from fat tissue which is terminally differentiated. It is also known as a lipocyte or fat cell, and specializes in storing energy as fat. In their differentiated state, adipocytes assume a rounded morphology associated with cytoskeletal changes and loss of mobility. Neural cells refer to cells of the nervous system and in particular of the brain. Examples of neural cells include, but are not limited to, neurones, astrocytes and oligodendrocytes. Endothelial cells refer to a thin, flattened cell, of which a layer of the cells lines the inside surfaces of body cavities, blood vessels and lymph vessels, making up the endothelium. The term "epithelial cell" refers to a cuboidal-shaped, nucleated cell which is generally located on the surface of a tissue. A layer of epithelial cells generally functions to provide a protective lining and/or surface that may also be involved in transport processes. The term "keratinocyte" refers to skin cells having the capability to produce keratin, including for example, cells known as basal cells, prickle cells, spinous cells, and granular cells. A hepatocyte is a cell that constitutes the main functional cells of the liver, and may constitute 60% to 80% of the mass of a liver tissue. Hepatocytes perform critical metabolic, endocrine, and secretory functions, which includes the synthesis of carbohydrates, cholesterol and bile salts, to name a few. Myocte refers to a differentiated, post-mitotic, muscle cell that has not undergone fusion and represents a transient cell type under most conditions. Cell from joint ligament may comprise a chondrocyte or a fibroblast from the articular ligament, peritoneal ligament or fetal remnant ligant, which are important as ligaments connect a bone to another bone to form a joint which is required for mobility. Cells from the nucleus pulposis have chondrocyte-like features. In an adult human, the cells of the nucleus pulposis obtain nutrients and eliminate waste by diffusion through blood vessels in the endplates of the vertebrate adjacent to the intervertebral discs. A HEK 293 cell is a human embryonic kidney cell line, and PER.C6® cell is a human retina cell line.

In alternative embodiments, the eukaryotic cell may be a non-anchorage dependent cell. Non-anchorage dependent cells may be further classified into Type A and Type B. Type A non-anchorage dependent cells refer to cells that are able to grow and multiply in the absence of a solid support material. For example, Type A non-anchorage dependent cells are able to proliferate in a suspension. Examples of Type A non-anchorage dependent cells include carcinoma cells used for regenerative medicine. Carcinoma cells used for regenerative medicine may include, but are not limited to hepato-carcinoma cells or pancreatic carcinoma cells. Type B non-anchorage dependent cells refer to cells that may grow and multiply when attached to a solid support material, and are also able to grow and multiply in the absence of a solid support material. Examples of Type B non-anchorage dependent cells include, but are not limited to chondrocytes, embryonic stem cells, adult stem cells, and endodermal lineage cells. For example, chondrocytes are able to proliferate in hydrogels, which are not considered as solid support materials. In the absence of adhesive moieties in the hydrogels, chondrocytes may adopt favorable spherical phenotype and undergo normal proliferation.

The term "chondrocyte" refers to a cell that is capable of expressing characteristic biochemical markers of chondrocytes such as, but not limited to collagen type II, chondroitin sulfate, and keratin sulfate, and is able to generate tissue or matrices with hemodynamic properties of cartilage in vitro. Stem cells refer to cells having self-replicating ability and also the ability to differentiate into at least two cells, and may be divided into totipotent stem cells, pluripotent stem cells and multipotent stem cells.

In various embodiments, the one or more species of living cells comprise chondrocytes. For example, the one or more species of living cells may consist essentially of or consist of chondrocytes. The one or more species of living cells may be at least substantially uniformly dispersed in the cell suspension.

Concentration of the one or more species of living cells may vary depending on the amount of hydrogel-forming agent present. In various embodiments, the amount of living cells in the cell suspension may be in the range from about $1\times10^3$ cells ml$^{-1}$ to about $1\times10^{10}$ cells ml$^{-1}$ of hydrogel-forming agent, such as about $1\times10^3$ cells ml$^{-1}$ to about $1\times10^7$ cells ml$^{-1}$, about $1\times10^5$ cells ml$^{-1}$ to about $1\times10^7$ cells ml$^{-1}$, about $1\times10^5$ cells ml$^{-1}$ to about $1\times10^{10}$ cells ml$^{-1}$, about $1\times10^7$ cells ml$^{-1}$ to about $1\times10^{10}$ cells ml$^{-1}$, about $1\times10^5$ cells ml$^{-1}$, about $1\times10^6$ cells ml$^{-1}$, about $1\times10^7$ cells ml$^{-1}$, or about $1\times10^8$ cells ml$^{-1}$. In some embodiments, the amount of living cells in the cell suspension is about $1\times10^7$ cells ml$^{-1}$ of hydrogel-forming agent.

The cell suspension comprising the one or more species of living cells and hydrogel-forming agent is then dispersed into an organic oil to form a microemulsion. By dispersing the cell suspension into the organic oil, the cell suspension is emulsified to form a microemulsion having an aqueous phase comprising the one or more species of living cells and the hydrogel-forming agent, and an oil phase comprising the organic oil.

The organic oil may be a mineral oil, or an oil of plant or animal origin. The term "mineral oil" as used herein refers to hydrocarbon oils derived from carbonaceous sources, such as petroleum, shale and coal or equivalents thereof. In preferred embodiments, the organic oil is an oil of plant or animal origin. Examples of organic oil that may be used include, but are not limited to, soya oil, corn oil, sunflower oil, rapeseed oil, cotton seed oil, peanut oil, olive oil, sesame seed oil, rice germ oil, fish oil, whale oil, palm oil, coconut oil, hemp oil, canola oil, wheat germ oil, safflower oil, linseed oil, tung oil, castor oil, and mixtures thereof. In various embodiments, the organic oil comprises soya oil. In some embodiments, the organic oil consists essentially of or consists of soya oil.

The terms "microemulsion" and "emulsion" as used herein are used interchangeably, and refer to a disperse system of two or more immiscible liquids. Therefore, emulsifying of one liquid in the other may result in formation of two different phases, in which small droplets of one liquid may be dispersed, i.e. separated and distributed throughout the space, in the other liquid. The small droplets of liquid is called the dispersed phase, while the other liquid, within which the small droplets of liquid is dispersed, is called the continuous phase.

Most microemulsions consist of water and oil or fat as immiscible phases. Depending on the composition and ratio of the phases, two distribution options exist. In case the aqueous phase, such as water "W" is the continuous phase and the oil "O" is the dispersed phase, the result is an "O/W emulsion" or oil-in-water emulsion, whose basic character is determined by the aqueous phase. If oil "O" is the continuous phase and water "W" the dispersed phase, the result is a "W/O emulsion" or water-in-oil emulsion, wherein the basic character is determined by the oil.

As mentioned above, in the method according to the first aspect, the cell suspension, which is aqueous-based, is dispersed into the organic oil, which is oil-based, to form a water-in-oil (W/O) emulsion. In some embodiments, the organic oil may contain a surfactant to stabilize the cell suspension dispersed therein to form the water-in-oil emulsion. For example, the surfactant may comprise or consist essentially of a hydrophobic surfactant. Examples of such surfactants include, but are not limited to, sorbitan ester, sorbitan monoester, sorbitan trioleate, sorbitan tristearate, sorbitan sesquioleate, sorbitan monolaurate, sorbitan monopalmitate, sorbitan monostearate, sorbitan monooleate, glycerol monooleate, glycerol monostearate, PEO/PPO copolymers, derivatives thereof, and mixtures thereof.

In various embodiments, dispersing the cell suspension into the organic oil is carried out under continuous stirring, or any form of dispersing method that is able to emulsify two different immiscible phases. Advantageously, use of continuous stirring allows size of microparticles formed to be controlled simply by varying the speed of stirring. Generally, a lower stirring speed results in a larger emulsion droplet size, and may translate into an increase in size of the microparticles formed. On the other hand, a higher stirring speed may result in a smaller microparticle. Accordingly, speed of stirring may be used to affect the size of microparticles formed.

Stirring speed as used herein may have a range of between about 150 rpm to about 2000 rpm, such as between about 150 rpm to about 1500 rpm, about 150 rpm to about 1000 rpm, about 300 rpm to about 2000 rpm, about 300 rpm to about 1500 rpm, about 300 rpm to about 1000 rpm, about 300 rpm to about 700 rpm, about 300 rpm, about 400 rpm, about 500 rpm, about 600 rpm or about 700 rpm. In various embodiments, continuous stirring is carried out at a speed of about 500 rpm. Depending on the type of materials used to form the cell suspension, for example, too low a stirring speed may result in an insufficient shear force for forming the microemulsion droplets.

Continuous stirring may be carried out for any suitable amount of time that is necessary to form the microemulsion. For example, the continuous stirring may be carried out for a few minutes, such as a time period in the range from about 1 minute to about 60 minutes, about 1 minute to about 30 minutes, about 1 minute to about 15 minutes, about 1 minute to about 10 minutes, about 1 minute to about 5 minutes, about 2 minutes to about 30 minutes, about 2 minutes to about 15 minutes, about 2 minutes to about 10 minutes, about 2 minutes to about 5 minutes, about 5 minutes to about 30 minutes, about 5 minute to about 15 minutes, about 5 minutes to about 10 minutes, or about 5 minutes, about 4 minutes, about 3 minutes, about 2 minutes, or about 1 minute. In various embodiments, dispersing the cell suspension into the organic oil is carried out under continuous stirring for about 2 minutes.

The method of the first aspect includes subjecting the microemulsion to conditions that allow the hydrogel-forming agent to form hydrogel microparticles comprising one or more species of living cells attached thereon and/or encapsulated therein. Advantageously, this allows incorporation of the one or more species of living cells to the hydrogel microparticles in a single step process, which translates into processing simplicity and efficiency. The one or more species of living cells may be loaded and localized within the microparticle, and may, additionally or alternatively, be present at the surface of the microparticle. In various embodiments, the one or more species of living cells are at least substantially uniformly dispersed within the hydrogel microparticle. In various embodiments, the hydrogel-forming agent that is comprised in the microemulsion is solidified to form the hydrogel microparticles.

In various embodiments, subjecting the microemulsion to conditions that allow the hydrogel-forming agent to form hydrogel microparticles comprising one or more species of living cells attached thereon and/or encapsulated therein comprises cooling the microemulsion, hence hydrogel-forming agent comprised therein, at a temperature in the range from about 0° C. to about 10° C., such as about 0° C. to about 8° C., 0° C. to about 6° C., 0° C. to about 4° C., 0° C. to about 2° C., 2° C. to about 10° C., 2° C. to about 8° C., 2° C. to about 6° C., 5° C. to about 10° C., 7° C. to about 10° C., or about 0° C., about 1° C., about 2° C., about 3° C., about 4° C., or about 5° C. In various embodiments, by cooling the microemulsion, the hydrogel-forming agent comprised in the microemulsion is gelled or solidified, thereby encapsulating the one or more species of living cells.

At the time of forming the hydrogel microparticles or after the hydrogel microparticles are formed, the organic oil may be extracted from the emulsion. For example, the organic oil and the hydrogel microparticles may be subjected to a separation process such as centrifugation, such that the organic oil is separated out from the hydrogel microparticles and which may be present as two phases, to allow ease of extraction of the organic oil from the microemulsion. The method of the first aspect may further comprise at least one centrifugation and at least one washing step after extracting the organic oil. The at least one centrifugation and the at least one washing step may serve as purification steps to clean for the microparticles formed for storage and/or application.

As used herein, the term "microparticle" refers to a microscopic particle having a size measured in micrometers (μm). Size of the microparticles may be characterized by their maximal dimension. The term "maximal dimension" as used herein refers to the maximal length of a straight line segment passing through the center of a microparticle and terminating at the periphery. In the case of microspheres, the maximal dimension of a microsphere corresponds to its diameter. The term "mean maximal dimension" refers to an average or mean maximal dimension of the microparticles, and may be calculated by dividing the sum of the maximal dimension of each microparticle by the total number of microparticles. Accordingly, value of maximal dimension may be calculated for microparticles of any shape, such as microparticles having a regular shape such as a sphere, a hemispherical, a cube, a prism, or a diamond, or an irregular shape.

The maximal dimension of the hydrogel microparticle formed may be in the range from about 50 μm to about 200 μm, such as between about 50 μm to about 150 μm, about 50 μm to about 100 μm, or about 50 μm to about 75 μm. In various embodiments, the hydrogel microparticles formed are essentially monodisperse.

In a second aspect, the invention relates to a composition comprising a mixture of a degradable hydrogel and at least one hydrogel microparticle comprising one or more species of living cells attached thereon and/or encapsulated therein according to the first aspect. The invention also relates in a further aspect to a composition comprising a mixture of a degradable hydrogel and at least one hydrogel microparticle comprising one or more species of living cells attached thereon and/or encapsulated therein, wherein at least one of the degradable hydrogel and the hydrogel microparticle comprises a porogen agent that effects degradation of the hydrogel microparticle As used herein, the term "degradable hydrogel" refers to a hydrogel having a structure which may decompose to smaller molecules under certain conditions, such as temperature, abrasion, pH, ionic strength, electrical voltage, current effects, radiation and biological means.

Thermal degradation refers to the use of heat to apply to a material such that it decomposes into smaller molecules. Abrasion degradation or physical degradation refers to the application of force or pressure on the material so as to break down the material into smaller components. Chemical degradation refers to use of a chemical reagent which degrades a material such as hydrogel into smaller molecules through effects of pH or ionic strength of the solution, or through chemical reaction with the material. For example, a form of chemical degradation can be hydrolytic degradation, wherein gelatin undergoes hydrolytic degradation in the presence of water, and can form a product called collagen hydrolysate (CH), which can contain peptides with a mean molecular weight of 3-6 kDa.

Electrical degradation refers to use of electrical current and/or voltage to pass through the material such that the material is decomposed. In radiation degradation, electromagnetic waves such as gamma and ultraviolet waves are used to degrade the material. The degradable hydrogel may also be degraded biologically, i.e. it is biodegradable. The term "biodegradable" refers to a substance which can be broken down by microorganisms, or which spontaneously breaks down over a relatively short time (within 2-15 months) when exposed to environmental conditions commonly found in nature. For example, gelatin can be degraded by enzymes which are present in the body.

In some embodiments, degradation of the degradable hydrogel may take place over a time period ranging from a few seconds to a few days or months. The time period required for the hydrogel to degrade may depend on a few parameters, for example, constituent of hydrogel, such as type of hydrogel precursors or hydrogel-forming agents used and water content of the hydrogel, degree of cross-linking, temperature, pH, amount of aqueous medium present, and pressure during gelation. Under physiological conditions, that means in an animal body, degradation is in general about 2 months. This period may be extended by subjecting the hydrogel to a cross-linking agent as described above.

The degradable hydrogel may form or act as a matrix or framework for the at least one hydrogel microparticle. In various embodiments, a plurality of hydrogel microparticles is present in the degradable hydrogel, and may be at least substantially uniformly dispersed within the degradable hydrogel matrix.

The degradable hydrogel may be formed of the same or different material as that of the hydrogel microparticle. In various embodiments, the degradable hydrogel is formed from a material that is different from that comprised in the hydrogel microparticle. The degradable hydrogel may be selected from the group consisting of hydrogels made from natural polymers, hydrogels made from synthetic polymers, and their combination thereof. Specific selection of the type(s) of polymers to form the degradable hydrogel may depend on the intended application, for example.

A "natural polymer" refers a polymeric material that may be found in nature. In various embodiments, hydrogels are formed by natural polymers selected from the group consisting of polysaccharides, glycosaminoglycans, proteins, and mixtures thereof. These hydrogels may also be termed herein as "natural hydrogels".

Polysaccharides are carbohydrates which may be hydrolyzed to two or more monosaccharide molecules. They may contain a backbone of repeating carbohydrate i.e. sugar unit. Examples of polysaccharides include, but are not limited to, alginate, agarose, chitosan, dextran, starch, and gellan gum. Glycosaminoglycans are polysaccharides containing amino sugars as a component. Examples of glycosaminoglycans include, but are not limited to, hyaluronic acid, chondroitin sulfate, dermatin sulfate, keratin sulfate, dextran sulfate, heparin sulfate, heparin, glucuronic acid, iduronic acid, galactose, galactosamine, and glucosamine.

Peptides, which form building blocks of polypeptides and in turn proteins, generally refer to short chains of amino acids linked by peptide bonds. Typically, peptides comprise amino acid chains of about 2-100, more typically about 4-50, and most commonly about 6-20 amino acids. Polypeptides generally refer to individual straight or branched chain sequences of amino acids that are typically longer than peptides. They usually comprise at least about 20 to 1000 amino acids in length, more typically at least about 100 to 600 amino acids, and frequently at least about 200 to about 500 amino acids. Included are homo-polymers of one specific amino acid, such as for example, poly-lysine. Proteins include single polypeptides as well as complexes of multiple polypeptide chains, which may be the same or different.

Proteins have diverse biological functions and can be classified into five major categories, i.e. structural proteins such as collagen, catalytic proteins such as enzymes, transport proteins such as hemoglobin, regulatory proteins such as hormones, and protective proteins such as antibodies and thrombin. Other examples of proteins include, but are not limited to, fibronectin, gelatin, fibrin, pectins, albumin, ovalbumin, and polyamino acids. For example, the polysaccharide may be selected from the group consisting of alginate, agarose, chitosan, dextran, starch, gellan gum, and mixtures thereof.

Examples of natural hydrogels which are well known in the art include alginate and agarose. In some embodiments, the degradable hydrogel comprises alginate. The term "alginate" refers to any of the conventional salts of algin, which is a polysaccharide of marine algae, and which may be polymerized to form a matrix for use in drug delivery and in tissue engineering due to its biocompatibility, low toxicity, relatively low cost, and simple gelation with divalent cations such as calcium ions ($Ca^{2+}$) and magnesium ions ($Mg^{2+}$). Examples of alginate include sodium alginate which is water soluble, and calcium alginate which is insoluble in water. In some embodiments, agarose may be used as the hydrogel. Agarose refers to a neutral gelling fraction of a polysaccharide complex extracted from the agarocytes of algae such as a Rhodophyceae. However, unlike alginate, it forms thermally reversible gels.

In various embodiments, synthetic hydrogels are selected from the group consisting of hydrogels made from a hydrophilic monomer, hydrogels made from a hydrophilic polymer, hydrogels made from a hydrophilic copolymer, and combinations thereof.

Examples of hydrophilic monomer that may be used include, but are not limited to, 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate, hydroxyoctyl methacrylate, acrylic acid, methacrylic acid, itaconic acid, fumaric acid, crotonic acid, maleic acid, monomethyl maleate ester, monoethyl maleate ester, monomethyl fumarate ester, monoethyl fumarate ester, (meth)acrylamide, crotonic amide, cinnamic amide, maleic diamide, fumaric diamide, methanethiole, ethanethiol, 1-propanethiol, butanethiol, tert-butyl mercaptan, pentanethiols, p-styrenesulfonic acid, vinylsulfonic acid, p-a-methylstyrenesulfonic acid, isoprene sulfonide and salts thereof.

Examples of hydrophilic polymer that may be used include, but are not limited to, polymers and oligomers of glycolide, lactide, polylactic acid, polyesters of a-hydroxy acids, including lactic acid and glycolic acid, such as the poly(a-hydroxy) acids including polyglycolic acid, poly-DL-lactic, poly-L-lactic acid, and terpolymers of DL-lactide and glycolide, e-caprolactone and e-caprolactone copolymerized with polyesters, polylactones and polycaprolactones including poly(e-caprolactone), poly(δ-valerolactone) and poly (gamma-butyrolactone); polyanhydrides, poly-orthoesters, other hydroxy acids, polydioxanone, collagen-hydroxyethylmethacrylate (HEMA), poly(hydroxylethyl methacrylate) (PHEMA), and other biologically degradable polymers that are non-toxic or are present as metabolites in the body. The above listed examples of hydrophilic polymers are also biodegradable.

As mentioned above, the degradable hydrogel may form or act as a matrix or framework for containing the at least one hydrogel microparticle. In various embodiments, a plurality of hydrogel microparticles is present in the degradable hydrogel, and may be at least substantially uniformly dispersed within the degradable hydrogel matrix.

The weight ratio of degradable hydrogel and at least one hydrogel microparticle in the composition may be of any ratio, such as between about 0.01 to 1, or about 0.25 to 1, or about 0.5 to 1, or about 0.75 to 1, or about 1 to 1.

In various embodiments, the hydrogel microparticle comprises a degradable material which degrades at body temperature. The term "body temperature" as used herein refers to the range of body temperatures expected for a living mammal, being from about 34° C. to about 40° C., and generally accepted to be about 37° C. for humans.

In various embodiments, the hydrogel microparticle comprises surface cross-linked gelatin. Suitable cross-linking agents that may be used to cross-link gelatin include genipin, formaldehyde, glutaraldehyde, 1-Ethyl-3-[3-dimethylaminopropyl]carbodiimide hydrochloride (EDC), N-hydroxysuccinimide (NHS), N-hydroxysulfosuccinimide (Sulfo-NHS), and mixtures thereof. For example, the gelatin may be cross-linked with a cross-linking agent such as genipin. In specific embodiments, the hydrogel microparticle comprises gelatin which is cross-linked in a 0.25 wt % genipin solution.

Degree of surface cross-linking may be influenced, for example, by varying the time of exposure of the degradable particle to the cross-linking agent, the ratio of cross-linking agent to hydrogel microparticle, and by varying the temperature and/or time during exposure of the hydrogel microparticle to the cross-linking agent. The temperature for cross-linking may be in the range from about 20° C. to about 40° C., such as about 25° C. to about 40° C., about 30° C. to about 40° C., about 35° C. to about 40° C., or about 35° C., about 36° C., about 37° C., about 38° C. or about 39° C. The temperature used depends on the kind of cross-linking agent and the polymer used for manufacturing the hydrogel microparticle.

At least one of the degradable hydrogel and the hydrogel microparticle comprises a porogen agent that effects degradation of the hydrogel microparticle. When present in the hydrogel microparticle, the porogen agent may be introduced into the hydrogel microparticle by incorporating the porogen agent in the cell culture medium used for cultivating the at least one species of living cells, and subsequently dispersing the living cells in the hydrogel microparticle. Presence of the porogen agent in the composition translates into a faster rate of degradation of the hydrogel microparticle compared to that of the hydrogel matrix. By the hydrogel microparticle degrading faster than the surrounding degradable hydrogel matrix, the one or more species of living cells may be released into the cavities formed by the degrading hydrogel microparticle, where they continue to proliferate. Advantageously, cavities that are formed in the degradable hydrogel matrix provide space for cell growth as well as allowing for improved nutrient and waste diffusion.

In various embodiments, the porogen agent comprises or consists essentially of an enzyme. Choice of porogen agent may depend on the type of hydrogel comprised in the hydrogel microparticle. For example, the porogen agent may be selected from the group consisting of a collagenase, a protease, a glycosidase, an actinase, a caseinase, a chondroitinase, a dermatanase, an elastase, a gelatinase, a heparanase, a hyaluronidase, a keratinase, a lipase, a metalloproteinase, a staphylokinase, a streptokinase, chymotrypsin, endopeptidase V8, trypsin, thermolysin, pepsin, plasmin, and combinations thereof. In some embodiments, the porogen agent comprises of collagenase. In specific embodiments, the porogen agent consists essentially or consists of collagenase.

Besides the concentration and type of porogen agent, the time period required for the hydrogel particle to degrade may also be dependent on different parameters, for example, constituent of hydrogel particle, such as type of degradable particle precursor used and water content of the hydrogel particle, degree of cross-linking, temperature, pH, amount of aqueous medium present, amount of pressure exerted by the degradable hydrogel matrix on the hydrogel particle, and pressure during gelation. In various embodiments, the hydrogel particle may be subjected to a heat treatment in order to degrade the hydrogel particle.

In addition to the one or more living cells that are comprised in the at least one hydrogel microparticle in the composition, the degradable hydrogel of the composition may also comprise one or more species of living cells. Depending on the intended application, the living cells that are contained in the degradable hydrogel may be the same as or different from the one or more species of living cells that are contained in the at least one hydrogel microparticle. Examples of living cells that may be used have already been described above. In various embodiments, the living cells that are contained in the degradable hydrogel comprise chondrocytes. In specific embodiments, the living cells that are contained in the degradable hydrogel consist essentially of or consist of chondrocytes.

The composition according to various aspects of the invention may be an injectable composition. In biological applications, for example, the injectability of the composition allows for ease of delivery into the site of intended usage. Following injection of the composition, the following steps may occur: (a) hydrogel matrix formation, (b) hydrogel particle degradation to form cavities in hydrogel matrix, (c) cell proliferation and migration within the hydrogel matrix, whereby the cells may be introduced from the hydrogel particle, or the hydrogel matrix and the hydrogel particle, into the cavities; (d) degradation of hydrogel matrix and tissue islet expansion. With tissue islet expansion, it is referred to cells which form on their own an extracellular matrix which replaces the hydrogel matrix.

In various embodiments, the hydrogel microparticle has a surface which provides additional reactive or functional groups that allow binding of further molecules. The term "reactive group" or "functional group" as used herein refers to a chemical moiety which exhibits bond formation capability. Examples of functional group include, but are not limited to, hydroxyl (—OH), carboxyl (—COOH), amide (—CONH—), thiol (—SH), or sulfonic (—SO$_3$H) groups, may further include other moieties, such as biotin, avidin, streptavidin, digoxigenin, and anti-digoxigenin. The term "binding" can mean physical bonding or chemical bonding.

Examples of other molecules include, but are not limited to, cells, biologically active molecules, particles, molecules, to name a few. In some embodiments, the hydrogel microparticle may have reactive groups that allow binding of cells on its surface. Therefore, in such embodiments, the cells which are bound may be present at the periphery of the hydrogel microparticle so that they may proliferate and grow at the cavity formed by the degrading microparticle, which may shorten the time at which tissues are formed since cells do not have to migrate through the hydrogel bulk to the cavity.

In some embodiments, the composition may be poured or injected into a mold having a desired anatomical shape, and then hardened to form a matrix having cells dispersed therein, which may be transplanted into a patient. The hydrogel may degrade, leaving only the resulting tissue. In some embodiments, the composition is adapted to be deliverable to a site, such as a defect site, in an animal or a human body. The composition may be injected directly into a site, such as a defect site, in a patient, where the hydrogel may harden into a matrix having cells dispersed therein. The hydrogels are also biocompatible, e.g., not toxic, to cells suspended in the hydrogel. It is also possible to let the hydrogel form and afterwards shape the composition to match the size and shape of a defect site in which it is to be implanted.

The composition according to the present invention may also serve as a cell growth medium or a cell construct. The cell construct may be incubated under conditions suitable for growth of the cells. That is, the cell construct may be placed in an incubator or into a patient so that the cells are maintained under adequate environmental conditions to permit the cells to survive, proliferate, differentiate and/or express certain products. "Cell growth" means that the cells survive and preferably, though not exclusively, divide and multiply. The composition may be adapted to induce tissue generation. In some embodiments, the composition may comprise cell growth media, which typically provides necessary nutrients and environmental conditions for cell growth. The cells may be introduced and incubated under conditions suitable for cell growth by introducing the composition into a patient and allowing native cells, such as stem cells to migrate into the composition. The composition may be administered by injecting the composition into the region requiring cellular growth or remodeling, such as a region of damaged tissue or a defect site.

In some embodiments, the composition according to the present invention may further comprise a biologically active molecule. As used herein, "biologically active molecules" are defined as those organic molecules having an effect in a biological system, whether such system is in vitro, in vivo, or in situ. Biologically active molecules may include, but are not limited to growth factors, cytokines, antiseptics, antibiotics, anti-inflammatory agents, analgesics, anesthetics, chemotherapeutic agents, clotting agents, metabolites, chemoattractants, hormones, steroids, and other drugs, or cell attachment molecules.

The term "growth factors" refers to factors affecting the function of cells such as osteogenic cells, fibroblasts, neural cells, endothelial cells, epithelial cells, keratinocytes, chondrocytes, myocytes, cells from joint ligaments, and cells from the nucleus pulposis. Platelet derived growth factors (PDGF), the transforming growth factors (TGF-.beta.), insulin-like growth factors (IGFs), fibroblast growth factors (FGFs), and the bone morphogenetic proteins (BMPs) are examples of growth factors encompassed in the composition according to the present invention. The term "cytokines" refers to peptide protein mediators that are produced by immune cells to modulate cellular functions. Examples of cytokines include, but are not limited to, interleukin-1β (IL-1β), interleukin-6 (IL-6), and tumor necrosis factor-α (TNFα).

The term "antiseptics" refers to a chemical agent that inhibits growth of disease-carrying microorganisms. Examples of antiseptics include peroxides, C6-C14 alkyl carboxylic acids and alkyl ester carboxylic acids, antimicrobial natural oils, antimicrobial metals and metal salts such as silver, copper, zinc and their salts. The term "antibiotic" includes bactericidal, fungicidal, and infection-preventing drugs which are substantially water-soluble such as, for example, gentamicin, vancomycin, penicillin, and cephalosporins. An antibiotic can be added, for example, for selection of the cells or to prevent bacterial growth in the composition. The term "anti-inflammatory agent" refers to any agent possessing the ability to reduce or eliminate cerebral edema (fluid accumulation) or cerebral ischemia, and can include examples such as free radical scavengers and antioxidants, non steroidal anti-inflammatory drugs, steroidal anti-inflammatory agents, stress proteins, or NMDA antagoists. The term "analgesics" refer to drugs which eliminate or alleviate pain without losing consciousness. Analgesics are generally classified, for example, into narcotic analgesics such as morphine, non-narcotic analgesics such as aspirin, and narcotic antagonistic analgesics which develop analgesic action through a mechanism similar to that of narcotic analgesics. The term "anesthetics" refers to an agent that produces a reversible loss of sensation in an area of a subject's body. Examples of anesthetics include bupivacaine, levobupivacaine, lidocaine, prilocalne, and cocaine.

The term "chemotherapeutic agents" refer to any natural or synthetic molecules that are effective against one or more forms of cancer, and may include molecules that are cytotoxic (anti-cancer agent), simulate the immune system (immune stimulator), or molecules that modulate or inhibit angiogenesis. Examples of chemotherapeutic agents include alkylating agents, antimetabolites, taxanesm, cytotoxics, and cytoprotectant adjuvants. The term "clotting agent" refers to refers to any molecule or compound that promotes the clotting of blood. Examples of clotting agents include a thrombin agent, which is commonly used as a topical treatment by vascular surgeons to stop surface bleeding after a large surface incision is made in the body, heparin, warfarin, and coumarin derivatives. The term "metabolite" refers to an intermediate or a product derived from enzymatic conversion of a substrate administered to a subject, the conversion occurring as part of a metabolic process of the subject. Examples of metabolite include glucose, carbohydrates, amino acids and lipids. The term "chemoattractants" refers to a substance that elicits accumulation of cells, such as chemokines, monocyte chemoattractant protein-1, and galectin-3. The term "hormone" refers to trace substances produced by various endocrine glands which serve as chemical messengers carried by the blood to various target organs, where they regulate a variety of physiological and metabolic activities in vertebrates. Examples of hormones include steroidal estrogens, progestins, androgens, and the progestational hormone progesterone. Steroids may also be classified as lipids. Naturally occurring steroids are hormones that are important regulators of animal development and metabolism at very low concentrations. Examples of steroids include cholesterol, cortisone, and derivatives of estrogens and progesterones. The term "cell attachment molecules" as used herein includes, but is not limited to, fibronectin, vitronectin, collagen type I, osteopontin, bone sialoprotein thrombospondin, and fibrinogen. Such molecules are important in the attachment of anchorage-dependent cells.

In a fourth aspect, the invention relates to a method of manufacturing a scaffold for tissue engineering.

As used herein, the term "scaffold" refers to a highly porous, artificial, three-dimensional network of interconnected pores that is used in vivo as a framework to which additional cells may attach and both existing and additional cells may grow to regenerate tissues, which may be lost through injury or disease. The term "living scaffold" refers to a scaffold that may be formed from and by living cells. One or more species of living cells may be attached to the scaffold via physical bonding or chemical bonding described herein. The living cells may be allowed to proliferate for a time period, in which the cells may grow to form colonies, after which the colonies may fuse to form a network of cells, and subsequently forming a living scaffold.

Generally, the time for proliferation may range from a few hours or days to a few weeks, such as about 1 day to about 4 weeks, or about 1 day to about 2 weeks, or about 1 day to about 1 week. The time for proliferation may also depend on the cultivation conditions for the cells. Parameters of the cultivation condition may include, for example, temperature, pH, amount of water, pressure, nutrients present, and type of cells. For example, it is known that eukaryotic mammalian cells grow much slower in general than for example prokaryotic bacterial cells. Cultivation conditions of cells are known in the art and may therefore be adapted by a person skilled in the art depending on the desired cell type and application.

The method comprises providing a composition comprising a mixture of a degradable hydrogel and at least one hydrogel microparticle comprising one or more species of living cells attached thereon and/or encapsulated therein. Examples of degradable hydrogel, hydrogel microparticle, and living cells that may be used have already been described above.

In various embodiments, the degradable hydrogel comprises one or more species of living cells. The composition is incubated under conditions which allow proliferation of the one or more species of living cells and degradation of the at least one hydrogel microparticle in the degradable hydrogel, to allow the one or more species of living cells that is present in the hydrogel microparticles, or the hydrogel microparticles and the degradable hydrogel, to proliferate and to allow the at least one hydrogel microparticle to degrade. The method also includes degrading the degradable hydrogel of the incubated mixture to obtain a scaffold.

The composition comprising the hydrogel microparticle and the degradable hydrogel may degrade naturally. The term "degrade naturally" refers to subjecting the composition in an environment of intended use such that the hydrogel is degraded. The composition may also be degraded artificially, using one of the degradation modes as described herein. The degradation rate of the hydrogel microparticle and the degradable hydrogel may be adjusted so as to suit the rate of cell proliferation. For example, the hydrogel microparticle may be degraded at a faster rate compared to that of the degradable hydrogel, both of which may take place faster than the rate of cell proliferation, so that the cells may have sufficient space for growth. It follows that the cavities in the degradable hydrogel may physically direct and accommodate the growth of neo-tissues inside the cavities. The neo-tissues may eventually fill the cavities, and may ultimately fuse together within the degradable hydrogel.

In various embodiments, at least one of the hydrogel microparticle and the degradable hydrogel comprises a porogen agent that effects degradation of the hydrogel microparticle. Examples of suitable porogen agents have already been mentioned above.

A hydrogel is characterized by a high permeability for exchange of nutrients necessary for cell proliferation, and the physical properties of hydrogels are similar to native tissue. As described above, different living cell species may be added into the hydrogel microparticle and/or degradable hydrogel depending on the type of tissue or organ for implantation. The term "tissue" refers to a structure formed by related cells joined together, wherein the cells work together to accomplish specific functions. An organ refers to a differentiated structure of an organism composed of various cells or tissues and adapted for a specific function. Therefore, one or more species of living cells may be added into or present in the composition to form a specific organ. For example, the heart which is an organ contains muscle tissue that contracts to pump blood, fibrous tissue that makes up the heart valves and special cells that maintain the rate and rhythm of heartbeats.

A scaffold according to the fourth aspect may be used for a wide variety of applications, e.g. tissue engineering. It may be used, e.g., for the three dimensional expansion of autologous cells like bone marrow mesenchymal stem cells which are limited due to donor site morbidity. The host for such applications may be any suitable animal. In a further embodiment, said host is a mammal or a human patient.

A scaffold according to the fourth aspect may also be used in transplantation as a matrix, for example, dissociated cells such as chondrocytes or hepatocytes to create a three-dimensional tissue or organ. Any type of cell may be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue may also be used, which may provide a number of different cell types in the same structure. The scaffold may also be used as a three dimensional in vitro culture system for attachment-dependent cells, e.g., hepatocytes in a three dimensional microenvironment which mimics the physiological microenvironment more closely.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

In an aspect, a therapeutic cell delivery methodology in the form of hydrogel encapsulating cell laden microspheres has been developed and investigated. In exemplary embodiments, as a model cell for cartilage tissue engineering, chondrocytes were successfully encapsulated in gelatin-based microspheres (mostly of diameter 50 μm to 100 μm, centred at 75 μm to 100 μm) with high cell viability during the formation of microspheres via a water-in-oil single emulsion process under a low temperature without any chemical treatment. These cell-laden microspheres were then encapsulated in alginate-based hydrogel constructs. By elevating the temperature to 37° C., the cell-laden microspheres were completely dissolved within 2 days, resulting in the same number of same-sized spherical cavities in hydrogel bulk, along with which the encapsulated cells were released from the microspheres and suspended inside the cavities to be cultivated for further development. In this cell delivery system, the microspheres played a dual role as both removable cell vehicles and porogens for creation of the intra-hydrogel cavities, in which the delivered cells were provided with both free living spaces and a better permeable environment. This temperature-cured dissolvable gelatin microsphere-based cell carrier (tDGMC) associating with cell-laden hydrogel scaffold was attempted and evaluated through WST-1, quantitative polymerase chain reaction, biochemical assays and various immunohistochemistry and histology stains. The results indicate that tDGMC technology can facilitate the delivery of chondrocytes, as a non-anchorage-dependent therapeutic cell, with significantly greater efficiency.

In a further aspect, a platform that makes use of degradable microspheres as cell carriers and porogens to create cavities for controllable sized hepatocellular spheroid development within the bulk of alginate hydrogel constructs according to various embodiments has been developed.

In exemplary embodiments, cells are first seeded onto genipin crosslinked microspheres and these cell-laden microspheres are encapsulated in alginate hydrogel. After gelation, microspheres are disintegrated via the introduction of collagenase (MMP9) so that cavities are made in the gel bulk; the loaded cells are suspended and entrapped in these cavities, providing space for spheroid formation while the alginate bulk serves as a confinement to restrict the size of spheroids generated within range.

The method according to various embodiments is advantageous in that the entire set-up is simple and does not require any specialized equipment. Furthermore, it is economic and convenient to scale-up. Particularly in embodiments wherein alginate is used as the hydrogel bulk, cellular spheroids could be recovered from the alginate gel bulk by sodium citrate treatment. Among the polysaccharide hydrogels, alginate is the only gel system that possesses this unique property for cell recovery. Hence, scaffold-free cellular aggregates could be harvested for further analysis or subsequent investigations.

Example 1.1: Fabrication and Size Characterization of tDGMC

Gelatin solution (5% w/v) was prepared by dissolving 0.50 g gelatin (gelatin type A from porcine skin; Sigma) in 10 ml solution consisting of 5 ml phosphate buffered saline (PBS) and 5 ml chondrocyte medium (CC medium). The composition of CC medium is as follows: DMEM Glutamax (Gibco) with 20% v/v FBS Gold (Gibco), 0.4 mM proline, 0.01 M 4-(2-hydroxyethyl)-piperazine-1-ethanesulfonic acid, 0.1 mM non-essential amino acids, 0.05 mg ml$^{-1}$ vitamin C, 100 mg ml$^{-1}$ streptomycin and 100 units ml$^{-1}$ penicillin.

Passage 1 porcine chondrocytes were suspended in 37° C. gelatin solution at a concentration of 1×10$^7$ cells ml$^{-1}$ gelatin. The suspension was added into a 50 ml beaker containing 15 ml soya oil (filtered and pre-warmed to 37° C.) and stirred for 2 min at 500 rpm at room temperature.

The beaker was then transferred into an iced water bath and stirred for 10 min at 300 rpm. The emulsion was centrifuged at 700 rpm for 3 min. After removing the supernatant, the pellet of gelatin microspheres with chondrocytes encapsulated within, named tDGMC, was resuspended in 15 ml 4° C. 1×PBS for washing. The suspension was centrifuged at 700 rpm for 3 min and washed again.

Figure 1:
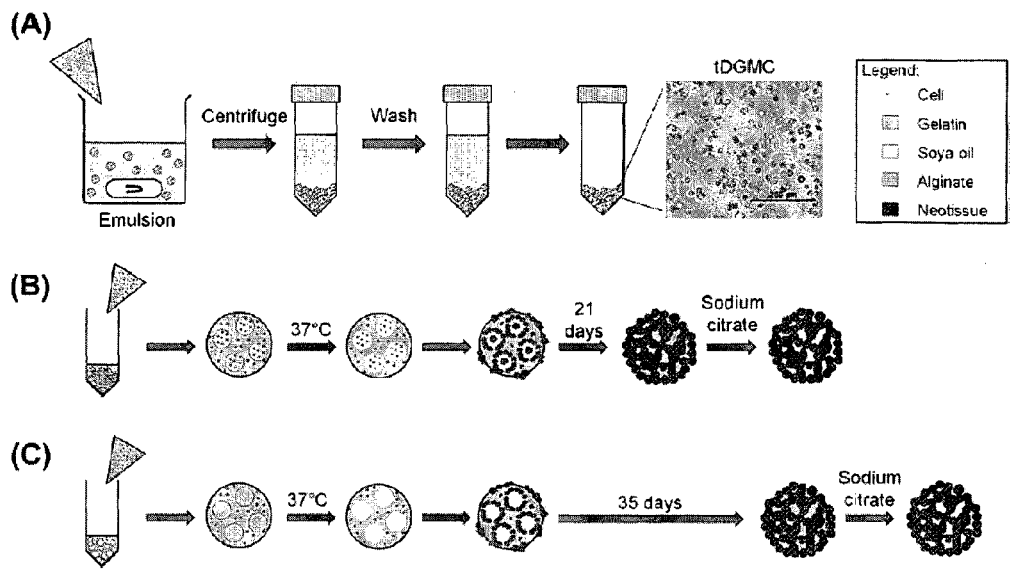
FIG. 1(A) to (C) are schematic diagrams of fabrication processes of tDGMC and constructs. In (A), fabrication process of tDGMC is depicted. Chondrocytes suspended in 37° C. gelatin type A solution are added to a beaker of 37° C. soya oil, and stirred in an iced water bath. The tDGMC-oil emulsion is centrifuged and then washed twice with 1×PBS. The PBS supernatant is subsequently removed. In (B), fabrication process of PTCC-tDGMC and LhCG-tDGMC is depicted. A suspension of chondrocytes in alginate is added to tDGMC (0.30 g ml$^{-1}$ alginate). The well-mixed suspension is then transferred to a silicon mould, and gelation of alginate is completed through the addition of calcium chloride solution to form PTCC-tDGMC. Upon incubation at 37° C., gelatin dissolves completely, and cavities are formed by the end of 2 days. Cells suspended within the cavities proliferate into cell islets, while cells from alginate gel bulk infiltrate cavities. Neotissues consisting of chondrocytes and their secreted ECM fill up the pores and merge together. LhCG-tDGMC is obtained by removal of alginate via sodium citrate (SC) treatment of PTCC-tDGMC construct after 21 days in culture. In (C), PTCC-blkMC and LhCG-blkMC fabrication process according to a state of the art process is depicted. A suspension of chondrocytes and blank gelatin microspheres in alginate is transferred into silicon moulds; gelation is as above. Cells from alginate bulk infiltrate cavities left behind by gelatin microspheres and neotissue develop. After 35 days of culture, alginate is removed via SC treatment to yield a scaffold-free 3-D LhCG-blkMC.

A brief schematic of the procedures, which were done under sterile conditions, is shown in FIG. 1A. A list of abbreviations used in sample naming is given in TABLE 1.

TABLE 1

List of abbreviations used.

| Abbreviation | Expansion |
|---|---|
| tDGMC | Temperature-cured dissolvable gelatin microsphere-based cell carrier |
| PTCC | Phase transfer cell culture |
| LhCG | Living hyaline cartilage graft |
| blkMC | Blank gelatin microspheres |
| blkGEL | Blank alginate gel |

For quantification of size distribution, tDGMC were suspended in a suitable amount of 1×PBS in a 100 mm petri dish. 20 random images were taken under light microscopy (Carl-Zeiss) for determination of size distribution.

Example 1.2: Fabrication of Three-Dimensional (3-D) Constructs (PTCC-tDGMC Constructs)

PTCC-tDGMC constructs were fabricated as shown in FIG. 1B. First, both 1×10$^7$ of passage 1 porcine chondrocytes and 0.30 g tDGMC were mixed into 1 ml alginate solution (1.5% w/v alginic acid dissolved in 0.15 M sodium chloride (NaCl)). Then, 80 μl of suspension was injected into each cylindrical silicon mould cavity, and the moulds were placed on a 100 mm petri dish pre-coated with calcium chloride ($CaCl_2$)-containing gelatin substrate (15% w/v gelatin and 102 mM $CaCl_2$ in distilled water). Each mould cavity was of 7 mm in diameter by 2 mm deep. For gelation of alginate to occur, the dish was placed in 4° C. for 4 min, after which 15 μl 102 mM $CaCl_2$ was gently added to the top surfaces of each construct and placed in 4° C. for 4 min again.

Upon incubation at 37° C., gelatin dissolved completely within 2 days, leaving behind chondrocytes suspended within the cavities, while chondrocytes were encapsulated within the alginate gel bulk. Suspended chondrocytes proceeded to proliferate into cell islets in the pores, while those in the alginate gel bulk proceeded to infiltrate the pores as well, forming neotissue consisting of chondrocytes and their secreted extracellular matrix (ECM). Given time, the neotissues continued developing and merged with one another.

Example 1.3: Fabrication of 3-D Constructs (PTCC-blkMC Constructs)

Blank (acellular) gelatin microspheres (blkMC) were prepared by an oil-in-water-in-oil double emulsion method. Briefly, 30 ml 10% w/v gelatin solution (preheated to 70° C.) was added to a 100 ml beaker containing 10 ml ethyl acetate and stirred at 700 rpm for 1 min. The gelatin/ethyl acetate emulsion was transferred to another 100 ml beaker containing 60 ml soya oil and stirred at 350 rpm for 1.5 min. Dioxane and acetone were used to wash the suspension three times to remove the soya oil. Finally, the gelatin microspheres were dried in a 70° C. oven and sieved for size quantification.

PTCC-blkMC constructs were then fabricated using blank gelatin microspheres. Briefly, wetted blank microspheres of diameters less than 200 μm were co-suspended with 1×10$^7$ of passage 1 porcine chondrocytes in 1 ml alginate solution at a concentration of 0.3 g ml$^{-1}$, and gelled as above (FIG. 1C). Upon culture at 37° C., the gelatin dissolved and formed pores within the constructs. Chondrocytes within the alginate gel bulk naturally proliferated towards the cavities and proceeded to fill up the pores with neotissue.

Example 1.4: Fabrication of 3-D Constructs (blkGEL-tDGMC Constructs)

tDGMC was suspended in alginate solution (without mixing with cells) at a concentration of 0.30 g ml$^{-1}$ alginate, injected into moulds and gelled as above. Blank alginate gel (blkGEL)-tDGMC constructs were used solely to observe the proliferation and viability of cells that had undergone the tDGMC technique.

Example 1.5: Fabrication of 3-D Constructs (Acquiring of Scaffold-Free Constructs of LhCG)

Each construct of PTCC-blkMC or PTCC-tDGMC was placed in a 15 ml tube containing 5 ml sodium citrate (SC) solution (55 mM in 0.15 M NaCl) for 10 min at room temperature to remove the alginate phase by dissolving and washing-off. This was done at weekly time points: days 14, 21, 28 and 35. After SC treatment, if the physical integrity was maintained from collapse, PTCC-blkMC and PTCC-tDGMC constructs were renamed LhCG-blkMC and LhCG-tDGMC, respectively.

All constructs were cultured in CC medium with gentle shaking (every alternate 12 h) on an orbital shaker at 50 rpm, 5% $CO_2$ and humidity at 37° C.

Example 1.6: Cell Viability Assays

The cell viability of the PTCC-blkMC and PTCC-tDGMC constructs was quantified by means of WST-1 assay (Roche, Switzerland).

Briefly, each sample was incubated in 10% v/v WST-1 reagent in CC medium for 1.5 h in the dark at 37° C., 5% $CO_2$. Medium was transferred to 96-well plate (Iwaki) and absorbance was measured at 450 nm against 690 nm reference absorbance by a microplate spectrum reader (Multiskan® spectrum, Thermo). Live/Dead staining (Invitrogen) was also used.

Example 1.7: Biochemical Analysis

Samples collected were frozen at −20° C. and lyophilized for 24 h prior to overnight digestion in 1 ml digestion solution consisting of 0.3 mg ml$^{-1}$ papain dissolved in 0.2 mM dithiothreitol and 0.1 mM disodium ethylene diamine tetraacetic acid. Hoechst 33258 assay was used to measure DNA content, which related to the number of chondrocytes (7.7 pg DNA per cell). Glycosaminoglycan (GAG) content was determined with dimethylmethylene blue assay, while total collagen content was measured using proline/hydroxyproline assay.

Example 1.8: Gene Expression Analysis Using Quantitative Real-Time Polymerase Chain Reaction All constructs were SC-treated to remove alginate before homogenization in 1 ml TRIzol® (Invitrogen), where applicable. RNA was extracted and converted to cDNA via reverse transcription. A quantitative real-time polymerase chain reaction (qRT-PCR) was executed with iQ™ SYBR® Green Supermix (Bio-Rad) and the iQ™ qPCR system (Bio-Rad). TABLE 2 lists the qRT-PCR primer sequences (AIT Biotech, Singapore) used in this experiment.

TABLE 2 qRT-PCR primer sequences for porcine gene markers: forward (F) and reverse (R).

| Gene | Accession No./Ref. | Sequence ID No. | Primer Sequences | Annealing temperature/° C. | Product size/base pairs |
|------|--------------------|-----------------|------------------|---------------------------|------------------------|
| Collagen Type 1 | [30] | 1 | F: 5'-CCTGCGTGTACCCCACTCA- 3' | 58 | 84 |
|  |  | 2 | R: 5'-ACCAGACATGCCTCTTGTCCTT- 3' |  |  |
| Collagen Type 2 | [31] | 3 | F: 5'-GCTATGGAGATGACAACCTGGCTC- 3' | 58 | 256 |
|  |  | 4 | R: 5'-CACTTACCGGTGTGTTTCGTGCAG- 3' |  |  |
| Aggrecan | [31] | 5 | F: 5'-CGAGGAGCAGGAGTTTGTCAAC- 3' | 58 | 177 |
|  |  | 6 | R: 5'-ATCATCACCACGCAGTCCTCTC- 3' |  |  |
| RhoA | NM_001664.2 | 7 | F: 5'-AGCTGGGCAGGAAGATTATG- 3' | 58 | 200 |
|  |  | 8 | R: 5'-TGTGCTCATCATTCCGAAGA- 3' |  |  |
| Integrin β1 | NM_002211.3 | 9 | F: 5'-TGCCAAATCATGTGGAGAATGTAT- 3' | 58 | 297 |
|  |  | 10 | R: 5'-GTCTGTGGCTCCCCTGATCTTA- 3' |  |  |
| Sox9 | NM_000346.3 | 11 | F: 5'-GCTGGCGGATCAGTACCC- 3' | 58 | 165 |
|  |  | 12 | R: 5'-CGCGGCTGGTACTTGTAA- 3' |  |  |
| Cartilage oligomeric matrix protein (COMP) | NM_007112.3 | 13 | F: 5'-GGCACATTCCACGTGAACA- 3' | 58 | 127 |
|  |  | 14 | R: 5'-GGTTTGCCTGCCAGTATGTC- 3' |  |  |
| TBP1 (Reference gene) | NM_001172085.1 | 15 | F: 5'-ACAGTTCAGTAGTTATGAGCCAGA- 3' | 58 | 152 |
|  |  | 16 | R: 5'-AGATGTTCTCAAACGCTTCG- 3' |  |  |

Ref [30]: Wynn R F et al., 2004, *Blood*, 104:2643.
Ref [31]. Jefferies D et al., 2002, *Vet Res*, 33:383-96.

For analysis, gene expression values relative to housekeeping gene TATA-binding protein (TBP) were calculated using the $\Delta C_T$ method, and subsequently normalized against the respective genes of PTCC-blkMC day 0 to obtain gene expression fold values. All reverse transcription and PCR reagents were purchased from Promega (Madison, Mich.), unless otherwise stated.

Example 1.9: Histology and Immunohistochemistry Staining

Paraffin-embedded PTCC-blkMC and LhCG-tDGMC samples from each time point were cut into 10-μm-thick sections using a microtome and subsequently mounted on glass slides. Sections were stained with hematoxylin and eosin (H&E), Masson Trichrome or Safranin O. Anti-IgG immunohistochemistry staining was performed for collagen types 1 and 2. Sections were incubated with primary antibody for collagen type 2 (2 μg ml$^{-1}$ in 1×PBS, MAB8887, Chemicon) at 4° C. overnight followed by anti-IgG (5 μgml$^{-1}$ in 1×PBS, AlexaFluor 488, Invitrogen) at room temperature for 1 h in the dark. In collagen type 1 immunohistochemistry staining, collagen type 1 primary antibody (2 μg ml$^{-1}$ in 1×PBS, goat polyclonal IgG, Santa Cruz Biotechnology), followed by anti-IgG (5 μgml$^{-1}$ in 1×PBS, AlexaFluor 543, Invitrogen) were used. To counterstain for nuclei, 40,6-diamidino-2-phenylindole (DAPI) was used.

Example 1.10: Statistical Analysis

All results are presented as mean±SD. Cell viability, biochemical and qRT-PCR data were compared against PTCC-blkMC constructs at the particular time points. ANOVA was used to measure statistically significant differences (p<0.05) between the groups (three samples per group).

Example 1.11: Results and Discussion—Establishment of tDGMC

In this study, tDGMC, which are chondrocyte-laden gelatin-based microspheres, were fabricated using a single water-in-oil emulsion method illustrated in FIG. 1A. When encapsulated in a hydrogel scaffold, tDGMC serve two purposes: as a cell delivery vehicle and as a porogen, since gelatin would completely melt and diffuse out of the scaffold within 2 days of incubation at 37° C.

Figure 2:
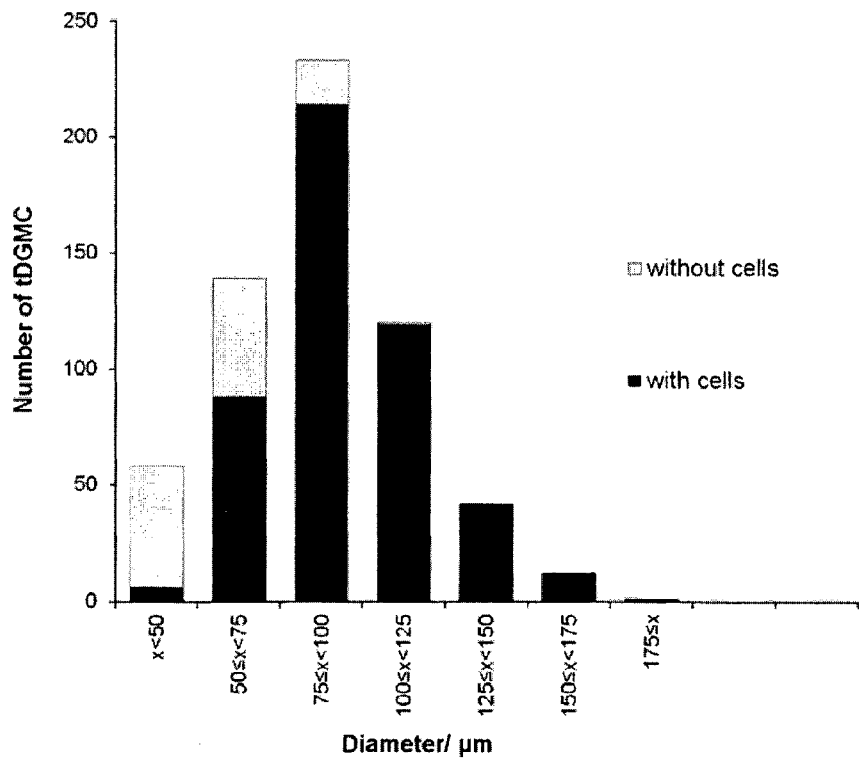
FIG. 2 is a graph showing tDGMC size distribution based on 20 random bright-field microscopy images. Y-axis: number of tDGMC; x-axis: diameter (µm).

The size distribution of tDGMC, based on manual counting of tDGMC in 20 random bright-field microscopy images, is presented in FIG. 2. tDGMC were mostly in the diameter range 50 µm to 125 µm centred at 75 µm to 100 µm. Larger tDGMC tend to have cells encapsulated within (a large proportion of black column) compared with those of smaller sizes. On one hand, the presence of cells in the tDGMC may induce a larger proportion of bigger microspheres fabricated; on the other hand, larger tDMGC also have a higher probability of containing cells. blkGEL-tDGMC constructs were fabricated for the sole purpose of easy observation of tDGMC alone in a 3-D environment. Previous work had studied the cell growth and development in the alginate gel phase; in the present work, cell growth and tissue development of the novel tDGMC was therefore studied without any background, i.e., acellular alginate gel phase. Through live/dead assays in FIG. 3A, the fabrication process was observed to be non-toxic to the cells. At day 0, the majority of cells were viable, albeit with some dead cells scattered throughout the construct. However, the cells were observed to have proliferated quickly to become cell islets with no necrotic cores by day 21. The dense cell islets had increased in size dramatically, notably in day 35, as the islets were about 500 µm min diameter, or approximately five to six times larger than average tDGMC at day 0. The islets had outgrown the cavity boundaries and into the alginate hydrogel, finally merging with other similarly dense cell islets.

Figure 3:
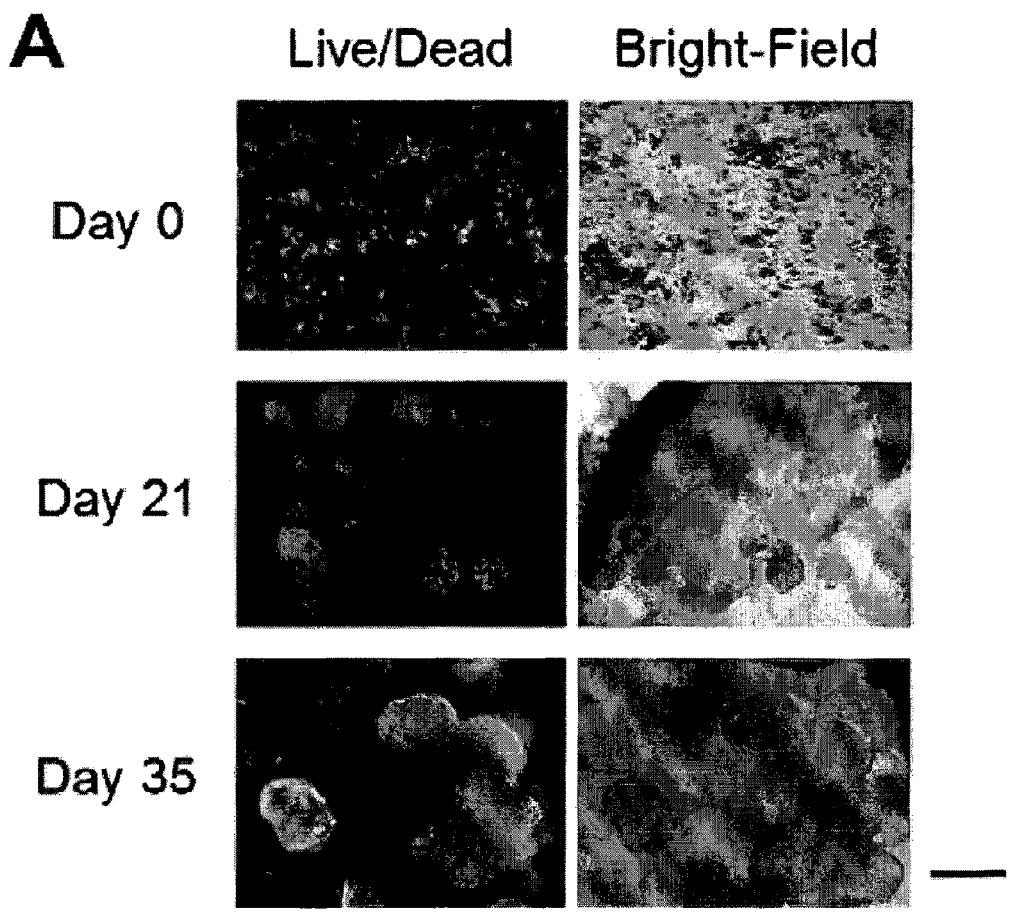
FIG. 3 shows viability assays of cells encapsulated in blkGEL-tDGMC. In (A), live/dead staining and corresponding bright-field microscopy images of tDGMC constructs at various time points at 4× magnification is shown. Scale bar represents 500 µm and applies to all images. (B) shows a graph of cell density normalized to dry weight of construct, based on DNA quantification using Hoechst 33258 assay. Y-axis: cell density ($\times 10^4$ per mg dry weight); x-axis: time (day).
Figure 3:
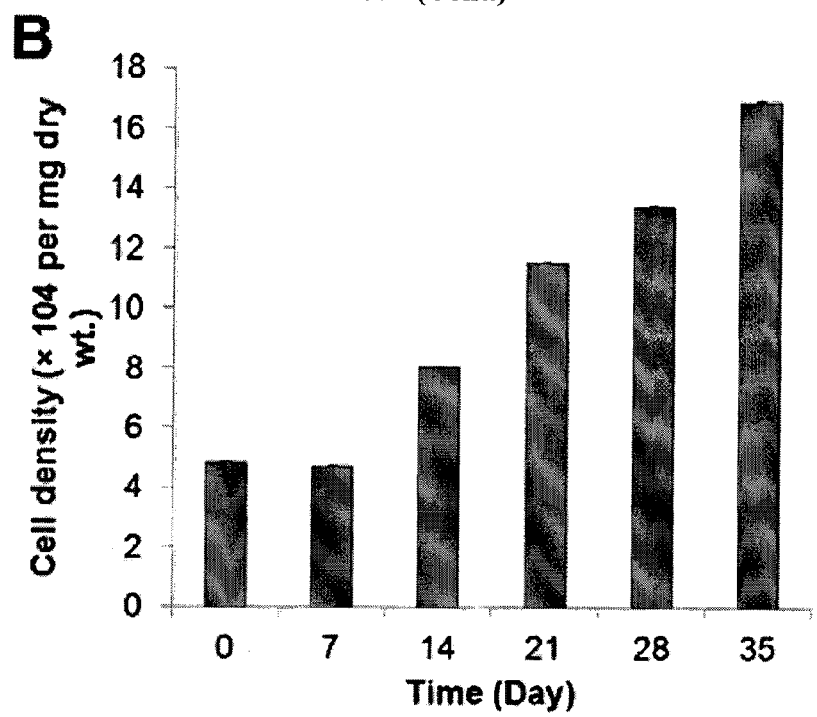

FIG. 3B shows the generally consistent increase in cell density (normalized to the dry weight) within blkGEL-tDGMC constructs over the 35-day period. At 35 days, there was more than 3.5 times as much cell density as the initial encapsulated cell density, although there was a slight decrease from day 0 to day 7. This could be due to the small amount of dead cells that have also been tabulated together at day 0, as well as the time required for the remaining viable cells to settle into the new scaffolding system. Nevertheless, both the qualitative (live/dead assays) and quantitative (DNA and therefore cell quantification using Hoechst 33258 assay) data consistently showed that cells encapsulated in tDGMC remained viable and were able to proliferate into dense islets of viable cells.

Based on the above, it may be seen that the fabrication process, which was simple, quick and free of chemical treatment, is non-toxic to chondrocytes.

Example 1.12: Results and Discussion—Application in PTCC System

The tDGMC technology was further applied using a PTCC approach for hyaline cartilage regeneration (FIG. 1B), where chondrocytes and tDGMC were co-encapsulated in an alginate hydrogel and named PTCC-tDGMC. The previously established PTCC approach used blank gelatin microspheres instead of tDGMC (thereby named PTCC-blkMC); after 35 days of culture, the alginate was removed from the construct to produce LhCG-blkMC, a scaffold-free construct composed of chondrocytes and their secreted ECM.

Figure 4:
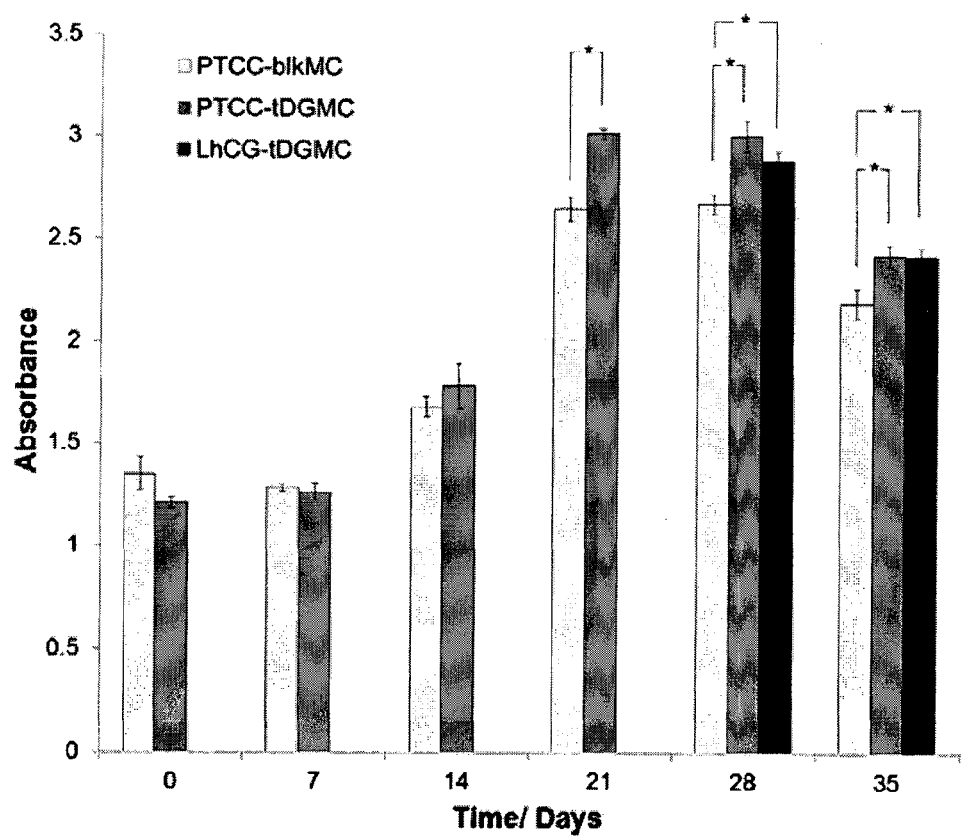
FIG. 4 is a graph showing assessment of cell viability through WST-1 assay. * indicates $p<0.05$; statistically significant differences between constructs were observed.

In the PTCC-blkMC constructs, blank gelatin microspheres played the role of porogens, which then created gel-medium boundaries within the alginate scaffold, to capitalize on the natural phenomenon that chondrocytes—as a type of non-anchorage-dependent cells—proliferated and formed neo-tissue quickly at the edges of non-cell adhesive gels (FIG. 1C). The replacement of blank gelatin microspheres with tDGMC not only created gel edges similar to those in the PTCC approach, but also provided extra chondrocytes suspended within the cavities left behind by the dissolved gelatin to be further cultured. Cell growth was then expected in two ways: outgrowth from alginate gel bulk into the cavities (as in the PTCC approach) and cell islet formation within the cavities (contributed by tDGMC). As seen in the WST-1 assay results in FIG. 4, PTCC-tDGMC constructs were able to proliferate and remain viable, with values significantly higher than PTCC-blkMC controls in the latter half of the experiment. This can be attributed to the increase in cell numbers in the PTCC-tDGMC constructs due to tDGMC. There was a general drop in absorbance values on day 35 from those on day 28; this could be explained by the lack of space within the constructs for further cell proliferation. It also correlated with why alginate was removed from PTCC-blkMC constructs on day 35 in previous studies. As absorbance values of PTCC-tDGMC constructs started decreasing from day 21 onwards, it was hypothesized that PTCC-tDGMC constructs had reached a similar cell-dense and ECM-rich state to those of PTCC-blkMC at day 35. Removal of alginate from PTCC-tDGMC and PTCC-blkMC constructs via SC treatment from day 14 onwards were done weekly and proved that by day 21, PTCC-tDGMC was able to retain its structural integrity with no visible debris and was thereby renamed LhCG-tDGMC, whereas PTCC-blkMC collapsed partially into several pieces (FIG. 15). PTCC-blkMC was only able to withstand the SC treatment on day 35, as previously established. WST-1 absorbance values of LhCG-tDGMC constructs were maintained with respect to PTCC-tDGMC constructs. From these results, the fabrication of a scaffold-free construct based on chondrocytes and their secreted ECM was accelerated by 40%, or 14 days.

Figure 5:
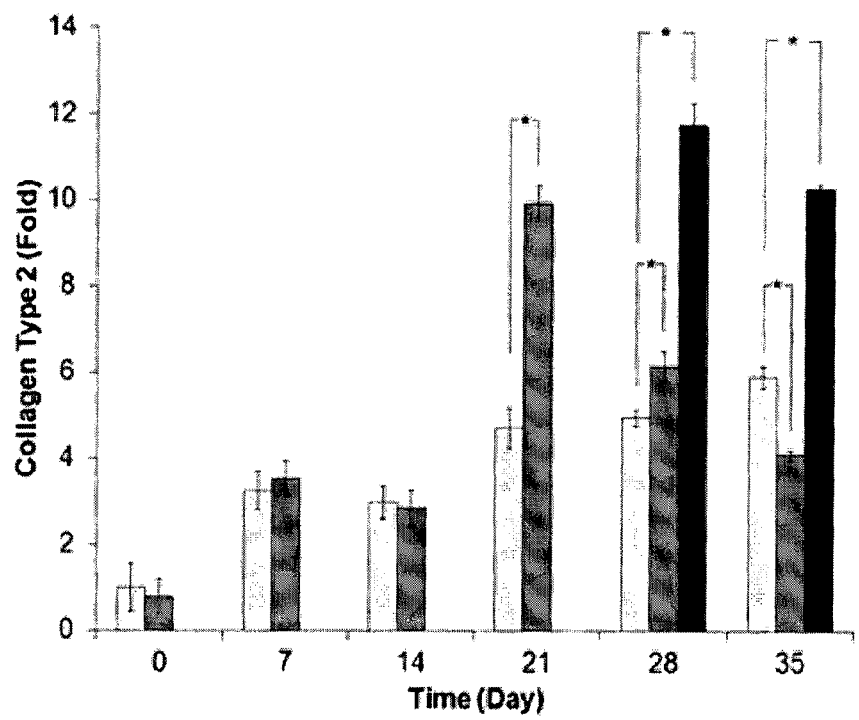
FIG. 5 shows graphs of analyses of various chondrocytic markers expression (A) collagen type 2; (B) collagen type 1; (C) Aggrecan; (D) Sox9; (E) COMP; (F) RhoA; (G) Integrin β1 for (i) PTCC-blkMC; (ii) PTCC-tDGMC; and (iii) LhCG-tDGMC. Y-axis: Fold; x-axis: time (day). Fold values for each gene were calculated based on the expression value of the particular gene in PTCC-blkMC construct at day 0. * indicates $p<0.05$; statistically significant differences between constructs were observed.
Figure 5:
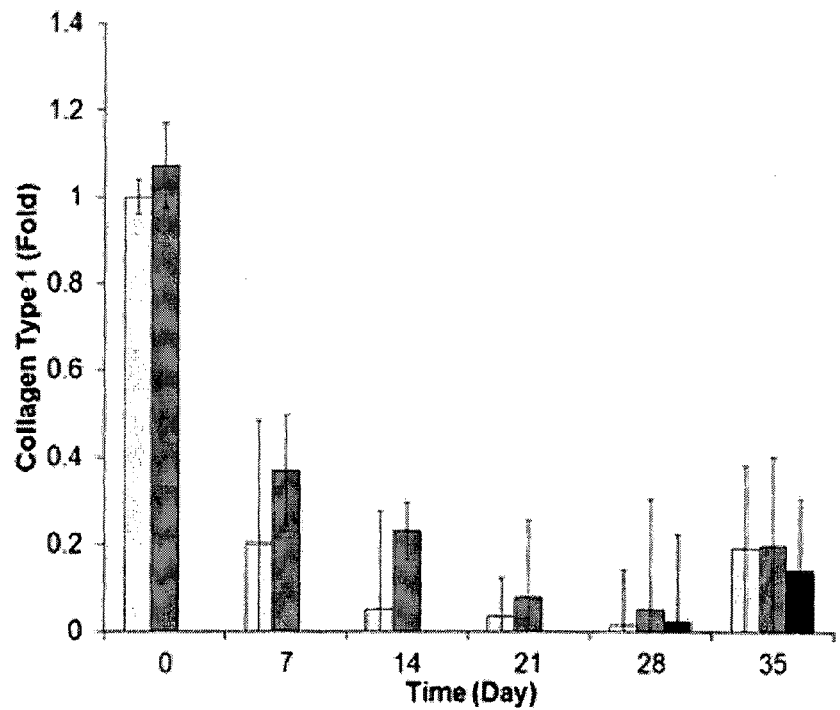
Figure 5:
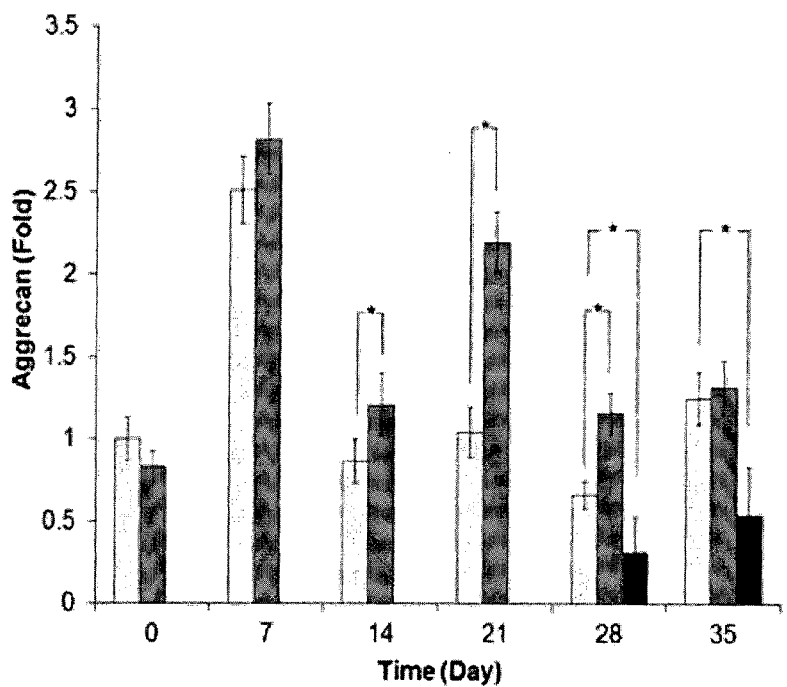
Figure 5:
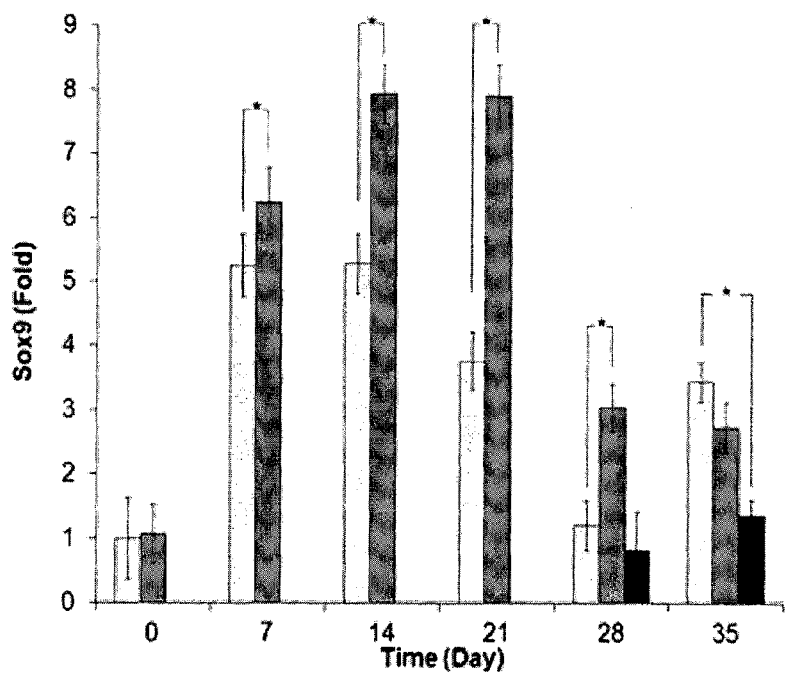
Figure 5:
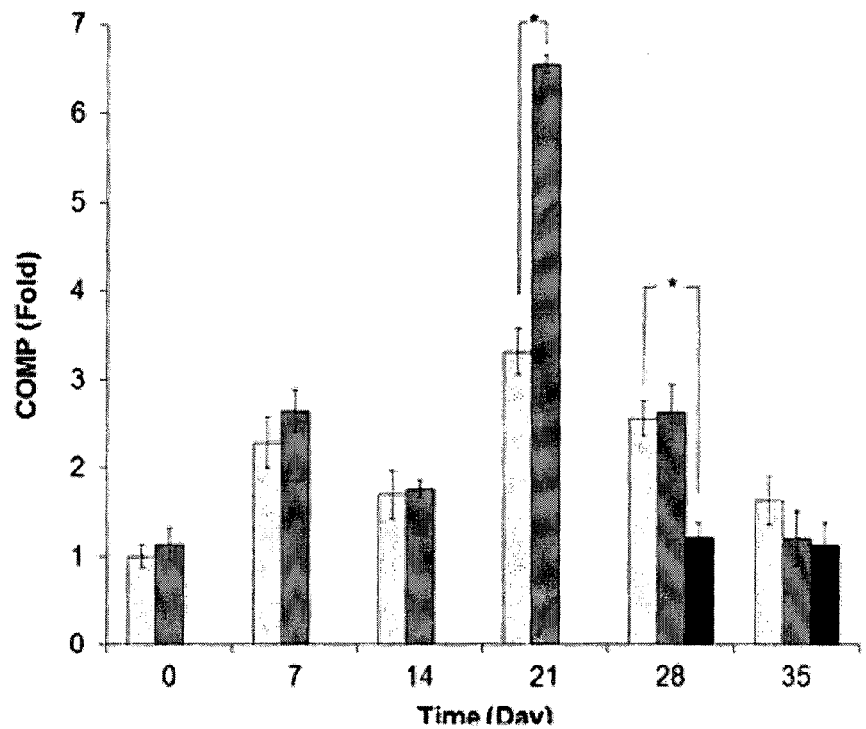
Figure 5:
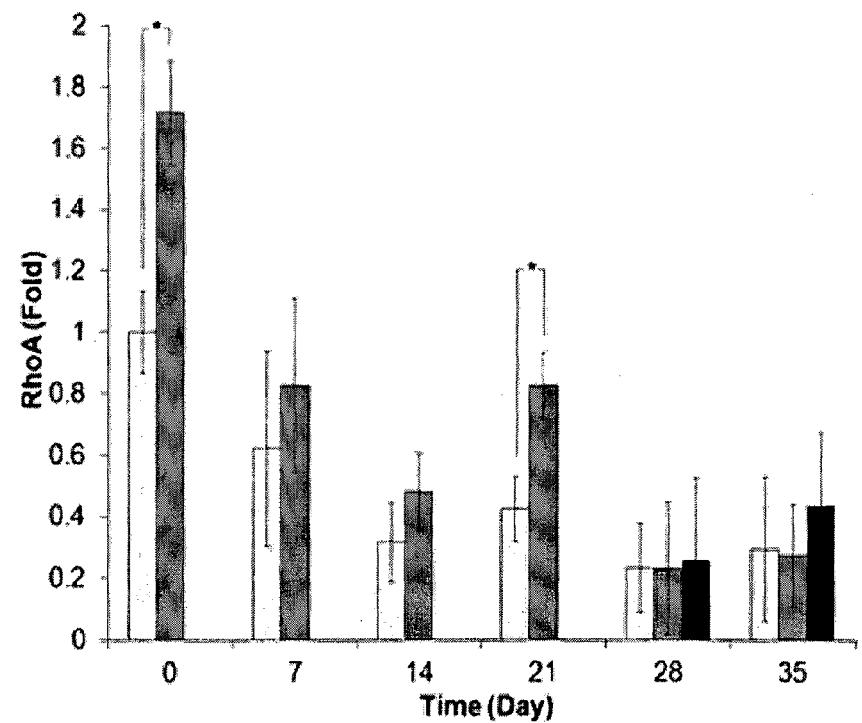
Figure 5:
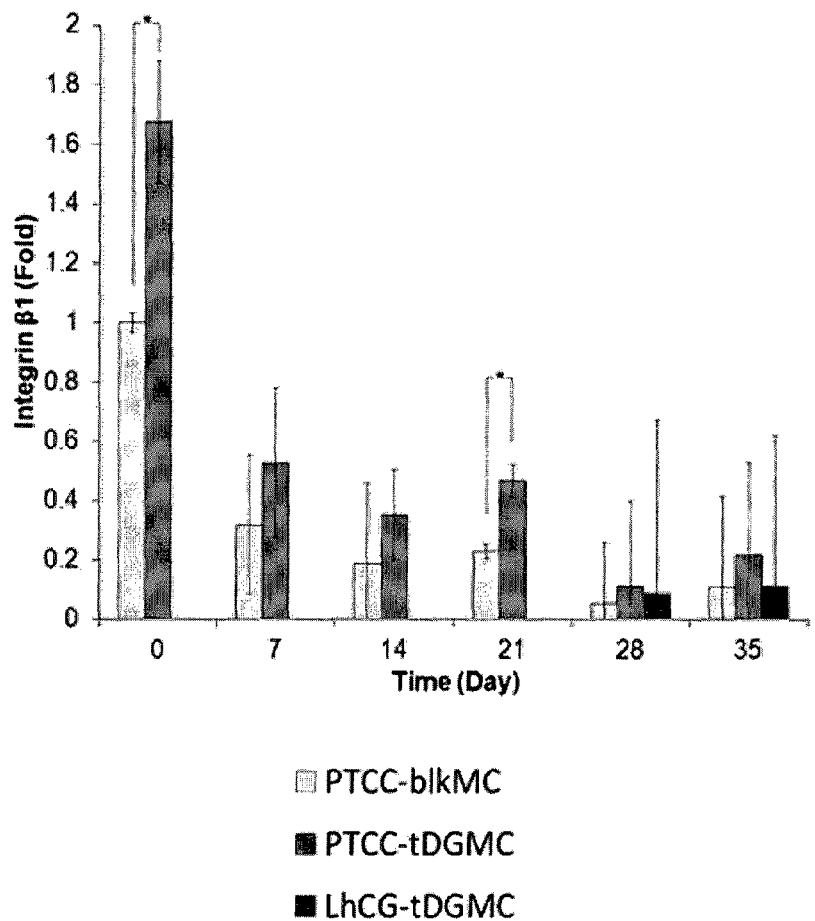

Gene expression studies were carried out via qRT-PCR to investigate chondrocytic markers (FIG. 5). All samples were normalized to that of control PTCC-blkMC day 0 for each gene, with PTCCblkMC day 0 designated a fold value of 1. Generally, cells expressed increasingly higher collagen type 2 with time for both PTCC-blkMC and PTCC-tDGMC constructs. On days 21 and 28, PTCC-tDGMC constructs had significantly higher collagen type 2 fold expressions than PTCC-blkMC; the former was approximately 6-8-fold higher than the control, whereas the latter had measured 4-5-fold. A suitable environment had been produced more quickly in the PTCC-tDGMC system, so cells were stimulated to produce hyaline cartilage-specific ECM, i.e., collagen type 2. The consecutive twofold drops in the PTCC-tDGMC system from day 21 to 35 could be explained by the space constraint and sufficient ECM detected by cells. This was further proven by the 10-12-fold high values measured in LhCG-tDGMC constructs: space left behind by alginate removal was detected by cells, which therefore became stimulated to produce ECM. However, collagen type 1 gene expression was constantly much lower than the control and had been depressed to <20% of the control on day 35. This was a favourable result, as collagen type 1, a major component of fibrosis, is minimal in hyaline cartilage ECM; the PTCC-tDGMC system was therefore inclined towards hyaline cartilage tissue development.

Generally, ECM components were highly expressed with time, with higher values for PTCC-tDGMC than PTCC-blkMC constructs especially during the latter half of the study period. Taken together, the PTCC-tDGMC system had expression patterns similar to those of PTCC-blkMC, albeit with higher tendencies towards hyaline cartilaginous tissue formation.

Figure 6:
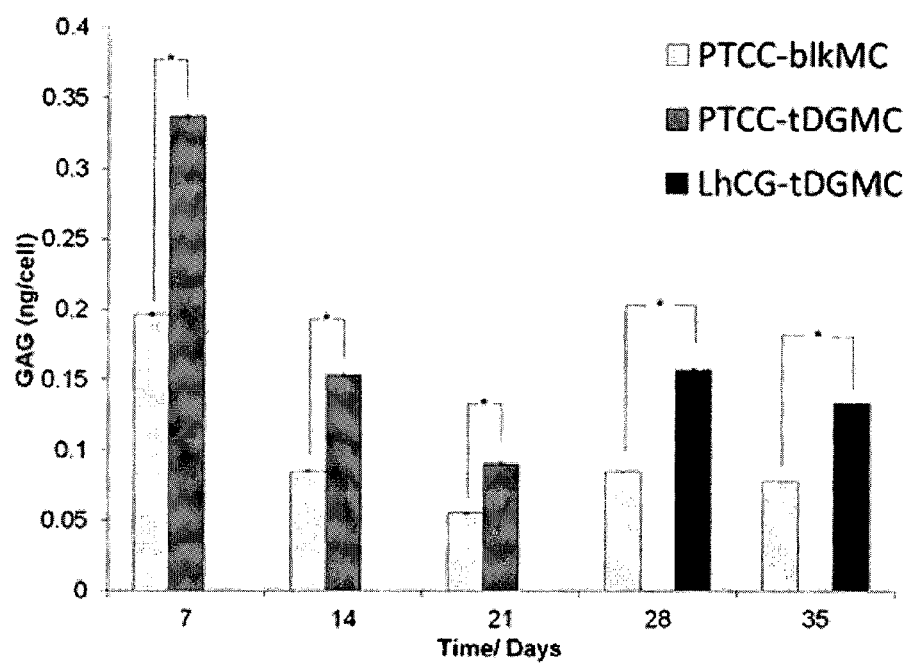
FIG. 6 are graphs showing biochemical analyses for GAG and collagen content plotted against time (day), wherein (A) and (B): GAG and collagen per cell; (C) and (D): GAG and collagen normalized to dry weight. * Indicates $p<0.05$; statistically significant differences between constructs were observed.
Figure 6:
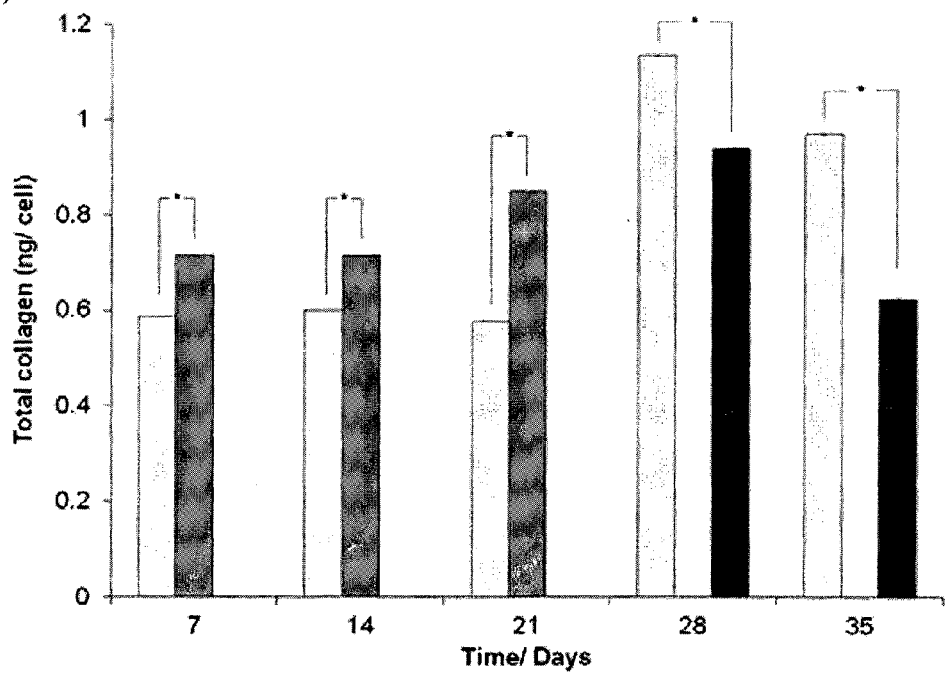
Figure 6:
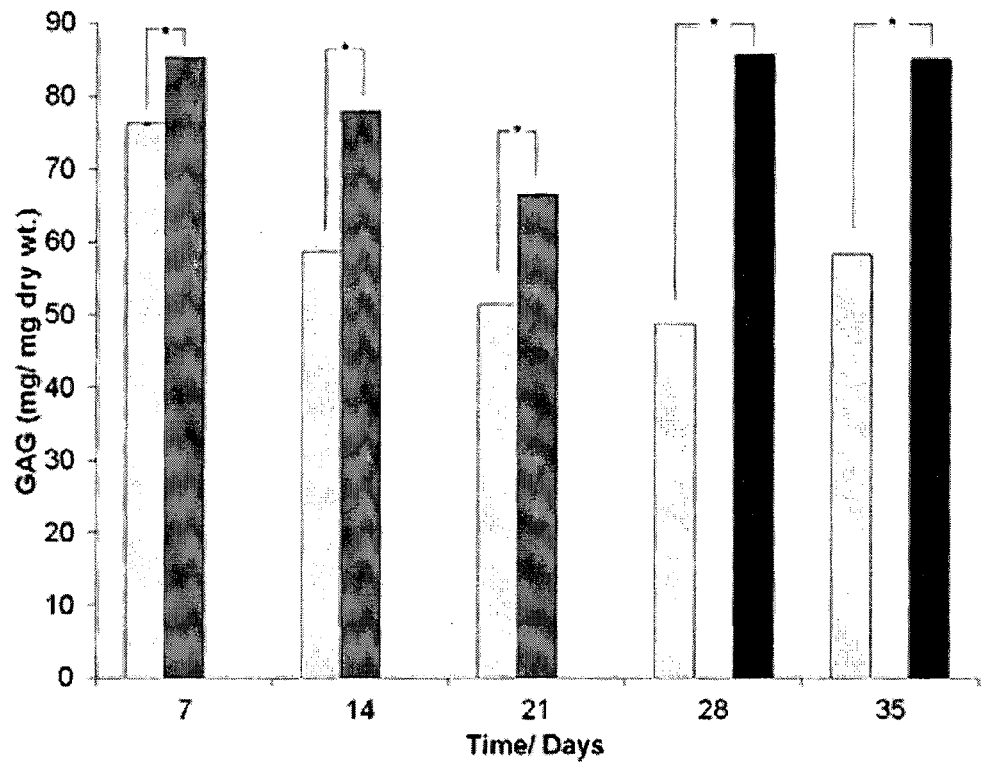
Figure 6:
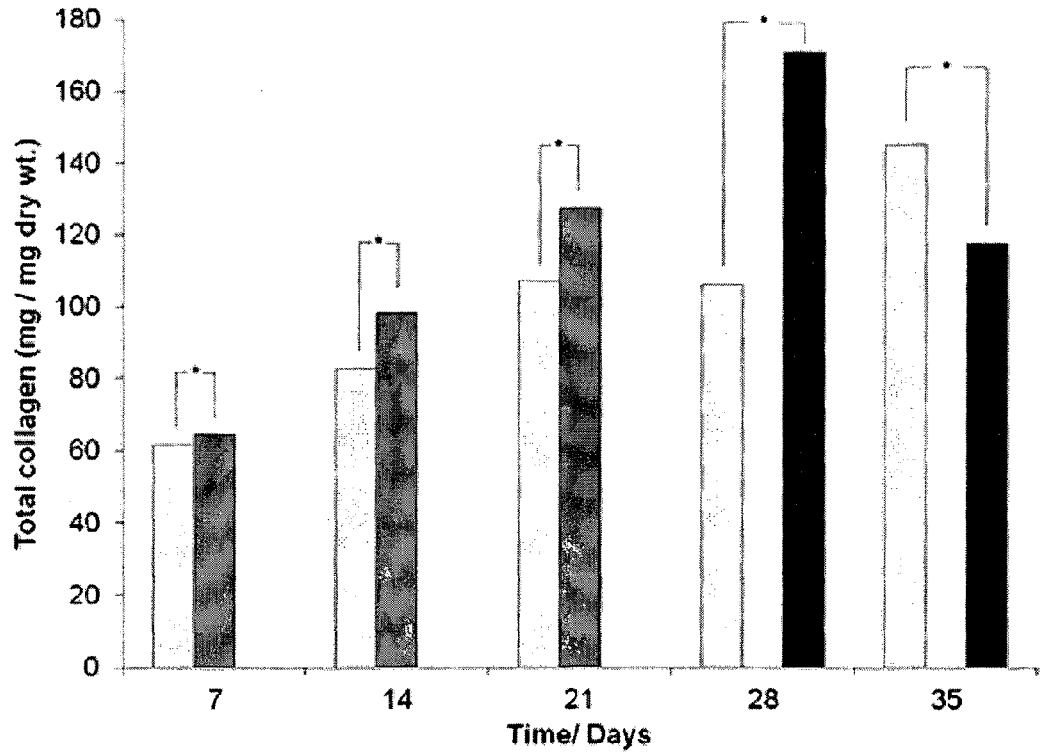

Two cartilaginous ECM components—GAG and collagen—produced in both systems were evaluated through biochemical assays (FIG. 6). The PTCC-tDGMC constructs consistently measured significantly higher amounts of GAG and collagen throughout the study period when compared against those of PTCC-blkMC. ECM components produced by cells were critical in maintaining the structural integrity of the construct after alginate was removed. As seen in total GAG and collagen content (FIGS. 6 (C) and (D)), PTCC-tDGMC day 21 reached a similar level of ECM components per unit construct's dry weight to day 35 for PTCC-blkMC constructs; therefore, alginate could be successfully removed from the PTCC-tDGMC constructs at that particular time without collapse in structure. While GAG content was evidently higher after alginate removal, i.e., for LhCG-tDGMC constructs, it was not as clear-cut for collagen content. Nonetheless, the overall results were promising, as there was an overall increase in ECM content, which therefore allowed for a purely scaffold-free cell-laden 3-D construct within 21 days of culture.

Figure 7:
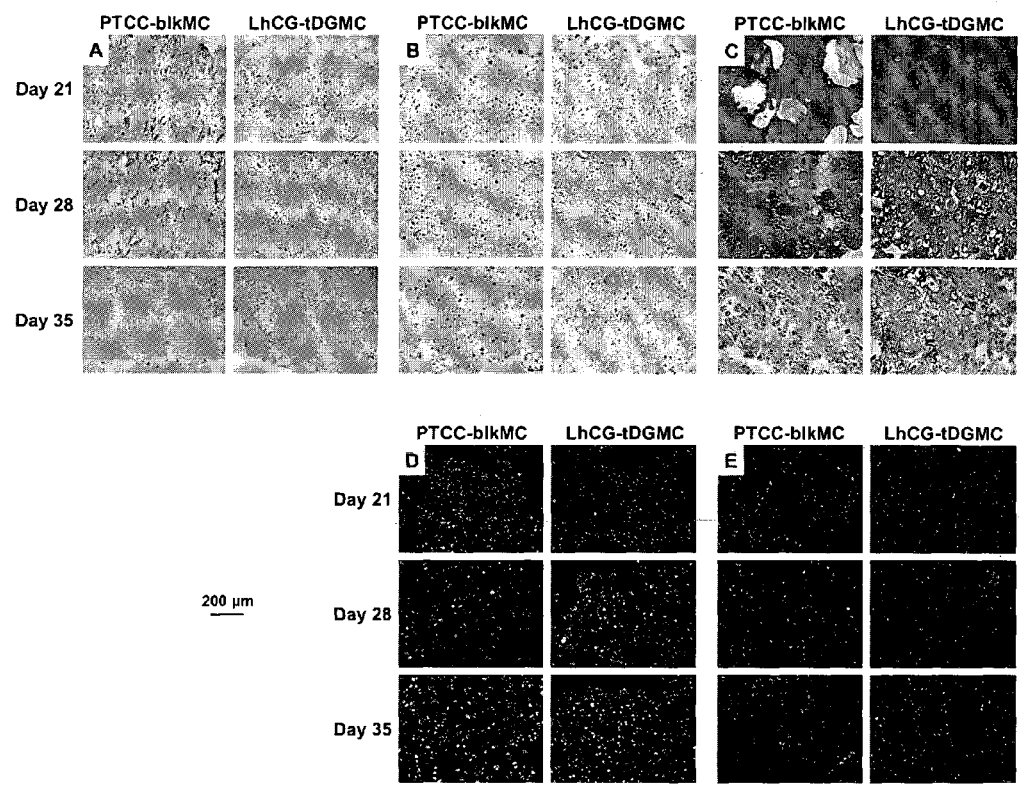
FIG. 7 shows various histochemical and immunohistochemistry staining comparing PTCC-blkMC and LhCG-tDGMC constructs at 10× magnification: (A) H&E staining; (B) Masson Trichrome staining; (C) Safranin 0 staining; (D) immunohistochemistry staining for collagen type 2; and (E) immunohistochemistry staining for collagen type 1. In all immunohistochemistry images, nuclei were stained blue (DAPI). Scale bar represents 200 µm and applies to all images.

Finally, a qualitative analysis of construct development towards a hyaline cartilage phenotype was done through various histological and immunohistochemistry stains (FIG. 7). LhCG-tDGMC constructs were typically visibly denser in terms of cell numbers and ECM content when compared against those of PTCC-blkMC constructs at similar time points; ECM was more equally distributed in the former (FIG. 7A). Furthermore, lacunae were observed more frequently and distinctively in LhCG-tDGMC constructs, which are also typically observed in hyaline cartilage tissues. These observations were further substantiated by Masson Trichrome (FIG. 7B) and Safranin 0 (FIG. 7C), which, respectively, stained blue for collagen and orange-red for proteoglycans. The darker blue stain surrounding the lacunae in LhCG-tDGMC in FIG. 7B and the uniform and darker orange-red Safranin 0 stained images in FIG. 7C implied that a denser ECM structure was secreted and modelled. On day 21 of FIG. 7C, especially, voids were observed in PTCC-blkMC construct, which could be attributed to the slow chondrocyte infiltration into the cavities left behind by gelatin microspheres.

This phenomenon, however, was unseen in LhCG-tDGMC at the same time point and could be explained by tDGMC's delivery of viable cells into the cavities. Collagen type 2 was abundant in both PTCC-blkMC and LhCG-tDGMC constructs, but visibly more compact in the latter (FIG. 7D), while collagen type 1 was negligible in both (FIG. 7E), supporting the gene expression studies and biochemical assays that tDGMC had accelerated the formation of a dense scaffold-free hyaline cartilaginous tissue.

tDGMC, when combined with the previously established PTCC approach, was shown to greatly aid hyaline cartilage regeneration. Cartilage-specific gene markers such as collagen type 2 were highly expressed and translated to higher ECM production, such that a scaffold-free construct (through removal of alginate) was realized as early as day 21 of culture. This was attributed to the higher viability and proliferation rates of cells, which also consistently produce markedly higher amounts of ECM per cell in the initial 21 days of culture. Favourably, fibrosis due to presence of collagen type 1 was consistently insignificant, as observed in both gene expression and immunohistochemistry. Therefore, tDGMC not only provided additional viable cells into the construct, the extra cells also retained their phenotype and contributed to hyaline cartilage regeneration. It is expected that in vivo experiments would yield favourable hyaline-like cartilage phenotype just as LhCG-blkMC had yielded in previous studies, except that LhCG-tDGMC would be fabricated within a much shorter duration (40% shorter).

tDGMC is therefore proven to be a viable cell delivery option, whose fabrication process of a single water-in-oil emulsion is simple, quick and free of chemical treatment. Through encapsulation in a hydrogel, tDGMC's gelatin component dissolves and diffuses out, leaving behind cells suspended in pores. The tDGMC therefore played a dual role as, first, a means of direct cell delivery and, second, a porogen to allow better diffusion of nutrients and waste within the alginate hydrogel scaffold. Cells were shown to be viable through Live/Dead staining assays, proliferating to fill up the pores as cell islets. Based on the success of this platform for cartilage development, this tDGMC technology can be envisaged to be broadened to encapsulate other non-anchorage-dependent cell types, such as hepatocytes, mesenchymal stem cells and pluripotent stem cells, since they have tendencies towards cell islet formation. In the case of stem cells especially, the potential to differentiate can also be used to develop tissues of a non-anchorage-dependent lineage.

This work has demonstrated a novel fabrication technique for cell-encapsulated gelatin microspheres, tDGMC, using porcine chondrocytes. Post-fabrication, the chondrocytes maximally remained viable and formed cell islets. When the platform was combined with a cell-laden gel bulk, it was shown to increase the scaffold's stability with heightened cell proliferation and hyaline cartilage-specific ECM production, thus accelerating the previously established PTCC approach of forming a dense scaffold-free construct LhCG, based solely on chondrocytes and its secreted ECM, by 40% or from 35 days to 21 days. Therefore, tDGMC technology was revealed to be able to facilitate delivery of chondrocytes into a gel bulk with significantly greater efficiency for hyaline cartilage regeneration. This promising platform is envisaged to be versatile for the delivery of similar non-anchorage-dependent cell types that have a tendency to form cell islets.

A simple and non-toxic water-in-oil single emulsion technique using cell-gelatin suspension and soya oil as exemplary embodiments was developed for manufacturing gelatin microspheres with non-anchorage-dependent cells: in this case chondrocytes. As shown above, gelatin microspheres would have then dissolved completely given a time window of 2 days at 37° C. incubation; the microspheres were therefore named temperature-cured dissolvable gelatin microsphere-based cell carriers (tDGMC). tDGMC is designed as a versatile platform for the delivery of non-anchorage-dependent cells such as hepatocytes, pancreatic β-cells, chondrocytes and pluripotent stem cells, all of which are naturally cell aggregate-forming. As chondrocytes were used in this experiment, tDGMC were used by combining with previously established phase transfer cell culture (PTCC) technology to ultimately construct a 3-D scaffold-free living hyaline cartilage graft (LhCG). Briefly, blank gelatin microspheres and chondrocytes are co-encapsulated in an alginate gel phase, in which the gelatin microspheres act as porogens. Chondrocytes tended to proliferate into and fill up the cavities left behind by gelatin to form neotissue within, by means of PTCC phenomenon. Given time, the neotissue islets further develop into the alginate gel bulk as well and merge with neighbouring islets to form a macroscopic cartilaginous construct whose structural integrity is no longer dependent on alginate. Alginate can be removed via chelation (immersion in sodium citrate (SC) solution) to obtain LhCG that is composed only of chondrocytes and their secreted extracellular matrix (ECM). Through implementation of tDGMC technology upon the PTCC system, it is envisioned that the LhCG formation process is accelerated to greatly convenience the clinical setting as a replacement for arthritic and damaged articular cartilage, in which tDGMC play two roles: creating cavities for better nutrient and waste diffusion and space for cell growth, as in the established PTCC system, while also delivering additional cells into the gel so as to accelerate development.

Example 2.1: Preparation of Genipin Crosslinked Gelatin Microspheres

Unless stated otherwise, all chemicals and reagents were purchased from Sigma Aldrich, Singapore. Gelatin microspheres were fabricated by the oil in water in oil (o/w/o) double emulsion method as described in our previous work. Briefly, 10 wt % gelatin solution was added to ethyl acetate at the ratio of 3:1 and the mixture was stirred at 700 rpm for 1 min, forming the first oil in water emulsion.

The second emulsion (o/w/o) was established by adding the mixture to edible oil at the ratio of 2:3. The final mixture was stirred at 350 rpm for 1.5 min before transferring to a cool water bath and maintained at the same stirring rate for another 15 min. The entire mixture was cooled in an ice-cold ethanol bath (about 20 min) for final microsphere solidification.

The microspheres were then washed with alternating dioxane and acetone solutions to remove the edible oil. The spheres collected were dried at 70° C. and sieved into various sizes.

To crosslink the microspheres with genipin, one gram of gelatin spheres (74 μm to 165 μm) was dispersed in 5 ml of 90% aqueous ethanol containing various concentrations (0.1 wt %, 0.25 wt % and 0.5 wt %) of genipin (Wako, Japan). The microspheres were kept in a 37° C. incubator for 16 h to allow crosslinking. The genipin crosslinked microspheres were then washed with pure ethanol three times before drying in the oven for 3 h at 100° C. All microspheres were sterilized with 10× penicillin/streptomycin (P/S) before hydrating in Dulbecco's modified eagle medium (DMEM) cell culture medium at 4° C. for long-term storage.

Example 2.2: Characterization of the Crosslinked Microspheres 0.05 g of genipin crosslinked microspheres crosslinked to various degrees was immersed in either 5 ml of phosphate buffer solution (PBS) at 4° C. or PBS containing matrix metalloproteinases 9 (MMP-9) at the concentration of 100 μg ml$^{-1}$ and were incubated at 37° C. for 30 min and 4 h respectively to determine their stability. The integrity of the microspheres was checked under a light microscope (Olympus IX71).

Example 2.3: Preparation of Cell-Laden Microspheres

Unless stated otherwise, all cell-related reagents were purchased from PAA Laboratories. The HepG2 cell was purchased from American Type Culture Collections (ATCC, Manassas, Va., USA) and were maintained in standard DMEM containing 1.5 mM L-glutamine, 10% (v/v) fetal bovine serum (FBS, 'Gold') and 100 units mg ml$^{-1}$ P/S at 37° C.

When HepG2 cells reached 70% to 80% confluence in the culture flask, they were detached by trypsin and re-suspended at a concentration of $5 \times 10^6$ cells ml$^{-1}$ with media. For the preparation of cell-laden microspheres, only those crosslinked in 0.25 wt % genipin solution was used. For every milliliter of cell suspension, 0.13 g of microspheres was added. 300 μl of the entire mixture was then added to each well of agarose gel pre-coated 24-well culture plate and kept in the incubator at 37° C. for 24 h to allow cell attachment to occur. The cell laden microspheres were then transferred onto a strainer of mesh size 40 μm (BD Falcon™) to facilitate media change.

Example 2.4: Fabrication of Cell-Laden Microspheres Hydrogel Composite with or without MMP-9

After cell-laden microspheres were cultured on the strainer for three days, they were encapsulated into alginate hydrogel to form the microcarrier-gel composite. As shown in the schematic illustration in FIG. 8A, three different groups were set up, namely; control, MMP-9 in media (MM) and MMP-9 in gel (MG).

Figure 8:
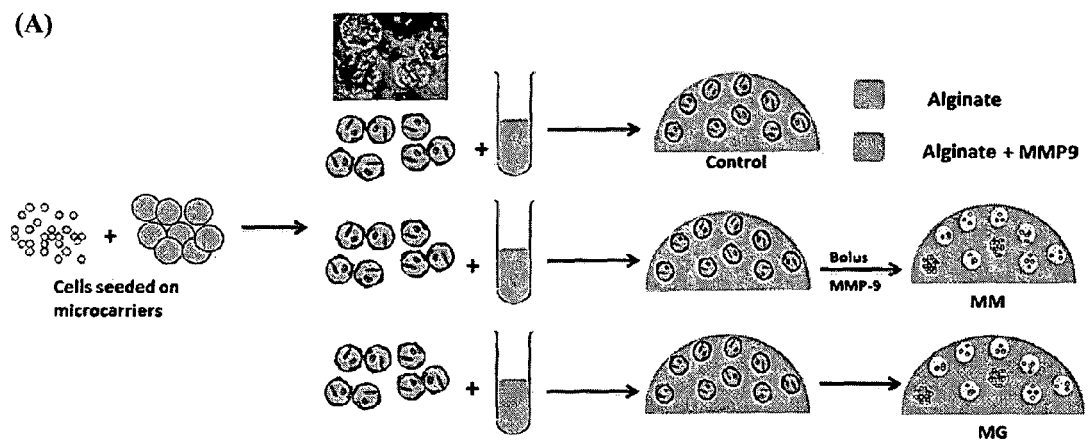
FIG. 8 (A) shows a schematic illustration of fabrication steps for cell-laden microsphere hydrogel composite construct (control, MM and MG); the inset is of 10× magnification; (B) Phase contrast images of control, MM and MG constructs with or without MMP-9 treatment. Scale bar denotes a length of 100 µm.
Figure 8:
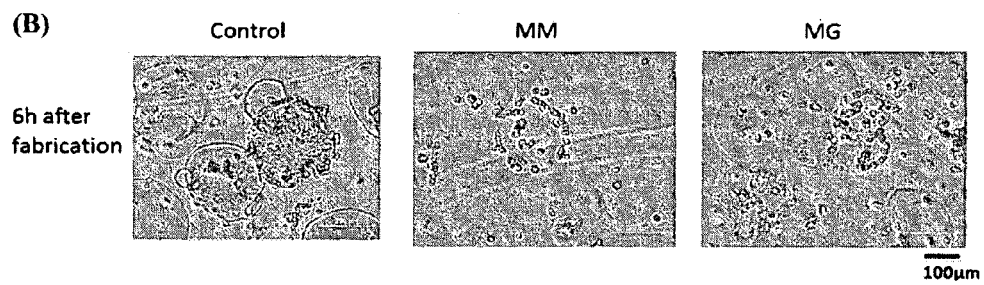

For the control and MM group, each milliliter of alginate solution (1.5 wt. % in 0.15 M NaCl) was gently mixed with 0.1 g of cell-laden microspheres. 85 μl of the mixture was injected into a circular mold (0=5 mm) and 102 mM of aqueous calcium chloride was added to facilitate gelation. The control constructs were cultured in standard DMEM, while MM group constructs were incubated in standard DMEM containing 100 μgml$^{-1}$ of matrix MMP-9. This concentration of MMP-9 is chosen based on our previous study where no acute toxicity was observed in HepG2 cells. As for the MG group, instead of normal alginate gel precursor solution, cell-laden microspheres were suspended in the same concentration of alginate precursor solution containing 100 μg ml$^{-1}$ MMP-9, during the fabrication of the constructs. MG constructs were cultured in standard DMEM just like the control. The day that the constructs were fabricated was noted as day 0. On day 1, culture media in all groups were changed and refreshed with standard DMEM without any MMP-9 and are shown in FIG. 8B.

Example 2.5: In Vivo Subcutaneous Implantation into Nude Mice

A total of six male Balb/c nude mice (4-week-old, mutant BALB/C, i-DNA Biotechnology Singapore) were used in this experiment. They were sedated using a combination of ketamine (40 mgkg$^{-1}$) and diazepam (5 mg kg$^{-1}$). Each mouse had three incisions made to create subcutaneous pockets for implantation and each received one day 1 construct from each group (control, MM and MG). The constructs were kept in the mice for 13 days before they were retrieved for histological examinations. All nude mice experiments were carried out in accordance with regulations of the Institutional Animal Care and Use Committees (IACUC), Nanyang Technological University (NTU), Singapore.

Example 2.6: Cell Viability and HepG2 Spheroid Morphology

All samples were tested for viability and proliferation at various time points throughout the 14 days of culture. Live/dead fluorescent staining (Invitrogen) was used where the cells were observed after 30 min incubation in calcein AM and ethidium homodimer-1. A total of three samples were collected from each sample group at each time point for WST-1 (Roche, Singapore) colorimetric assay. The samples were incubated at 37° C. for 1.5 h and the absorbance at 450 nm was measured with reference to 620 nm using a microplate reader.

Example 2.7: Albumin and Cytochrome P450 Gene Expressions

For each sample group, three constructs were pooled together and RNA was extracted using TRIzol® (Invitrogen). 500 ng of RNA from each group were used to convert to cDNA using reverse transcription kit (Promega), adhering strictly to protocol given by the supplier. Subsequently, they were analyzed quantitatively using a real-time polymerase chain reaction (RT-PCR). SYBR green iQ Buffer (Bio-Rad) was used to perform RT-PCR and the relative gene expressions were normalized to the housekeeping gene (β-actin) using $2^{-\delta C_T}$.

Here, $C_T$ represents the cycle number when an arbitrarily placed threshold was reached and $\delta C_T = (C_{T,target\ gene} - C_{T,\beta-actin})$. Primers with annealing temperatures and product sizes are listed in TABLE 3.

TABLE 3

List of primer sequence used for real-time PCT. A.T. denotes annealing temperature while P.S. denotes product size.

| Genes | Primer sequence (both 5'- 3') | Seq. ID No. | A.T (° C.) | P.S (bp) | Ref. |
|---|---|---|---|---|---|
| hβ-Actin | Forward: GTGGGGCGCCCCAGGCACCA | 17 | 58 | 540 | 26 |
|  | Reverse: CTCCTTAATGTCACGCACGATTTC | 18 |  |  |  |
| hCYP1A1 | Forward: TCTTTCTCTTCCTGGCTATC | 19 | 58 | 596 | 27 |
|  | Reverse: CTGTCTCTTCCCTTCACTCT | 20 |  |  |  |
| hALB | Forward: GTGGGCAGCAAATGTTGTAA | 21 | 58 | 188 | 19 |
|  | Reverse: TCATCGACTTCCAGAGCTGA | 22 |  |  |  |

Ref [26]: Nakazawa K et al., 2006, J. Biomater. Sci. Polym. Ed. 17 859-873
Ref [27]: Tostoes R M et al, 2011, Biotechnol. Bioeng. 108, 41-49
Ref [19]: Turner W S et al., J. Biomed. Mater. Res. B, 82, 156-168

Example 2.8: Albumin Quantification

Culture medium from each construct (n=3) was collected and replaced at various time points throughout the 14 days of culture. Media collected were stored at −20° C. before testing. Albumin concentrations in the media supernatant were determined colorimetrically with the commercial albumin test kit (Bio-Quant). The values obtained were averaged and normalized against the control on day 1.

Example 2.9: Histology Staining

All samples were fixed in 4% aqueous paraformaldehyde overnight before dehydrating in increasing concentrations of ethanol. The samples were embedded in paraffin and sectioned to a thickness of 8 μm. Subsequently, they were immersed in xylene to remove the paraffin and separately stained for H & E and 4',6-diamidino-2-phenylindole (DAPI) before viewing in a fluorescent microscope (Olympus IX71).

Example 2.10: Statistical Analysis

Where appropriate, ANOVA was performed to analyze results and P<0.05 was considered to indicate a statistically significant difference. Data are presented as mean with ±SD.

Example 2.11: Characterization of Genipin Crosslinked Gelatin Microspheres

To determine a suitable degree of crosslinking for the microspheres, three different concentrations of genipin solutions (0.1 wt %, 0.25 wt % and 0.5 wt %) were used to crosslink the gelatin microspheres.

Figure 9:
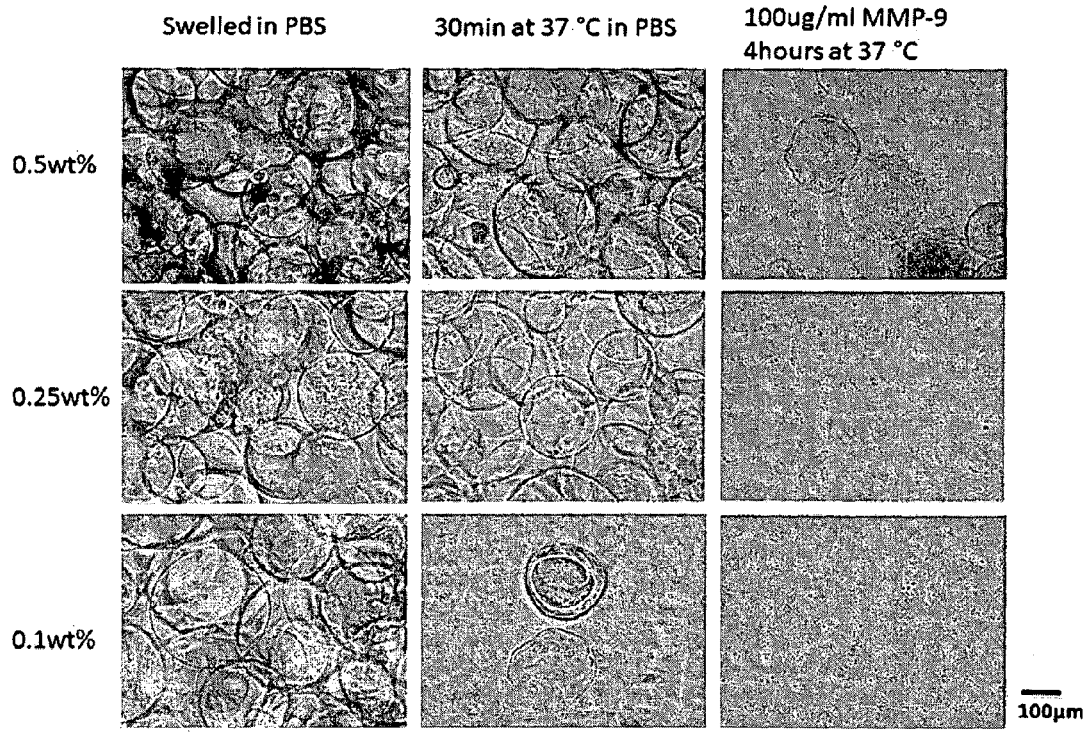
FIG. 9 shows overview of gelatin microspheres after crosslinking in different concentrations of genipin (0.1 wt %, 0.25 wt % and 0.5 wt %). First column: genipin crosslinked microspheres after swelling in PBS solution. Approximation of crosslink degree is indicated by the intensity of blue pigment formed. Second column: genipin crosslinked microspheres in PBS incubated at 37° C. for 30 min. Third column: genipin microspheres incubated in 100 µg ml$^{-1}$ MMP-9 containing media at 37° C. for 4 h. Scale bar denotes a length of 100 µm.

As shown in FIG. 9, spheres crosslinked in a higher concentration of genipin resulted in a greater intensity of the blue pigment formation, indicating a higher degree of crosslinking. After 30 min of incubation at 37° C., microspheres crosslinked in 0.1 wt % genipin solution dissolved while those crosslinked in 0.25 wt % and 0.5 wt % genipin remained intact. In the presence of MMP-9, microspheres crosslinked in 0.1 wt % and 0.25 wt % degraded after 4 h but those in 0.5 wt % could not degrade completely.

The desired properties of the microspheres in this study are present in 0.25 wt % crosslinked microspheres where they maintain their integrity under normal culture condition but readily degrade upon the introduction of MMP-9. For illustration purposes, only microspheres crosslinked in 0.25 wt % genipin were used for subsequent experiments.

Example 2.12: Cell Viability and HepG2 Spheroid Morphology in Constructs

HepG2 cells were cultured on 0.25 wt % genipin microspheres for three days before encapsulating them in alginate hydrogel. As mentioned, three different set-ups were made, namely; the control where it did not receive any MMP-9 treatment, MM where MMP-9 was added to the culture medium and lastly MG where MMP-9 was introduced via the alginate hydrogel (FIG. 8A).

As shown in FIG. 8B, 6 h after MMP-9 treatment, the microspheres within MM and MG constructs degraded, creating cavities of corresponding sizes. The cells which were originally attached on the microsphere now resided at the edge of the cavities created.

Figure 10:
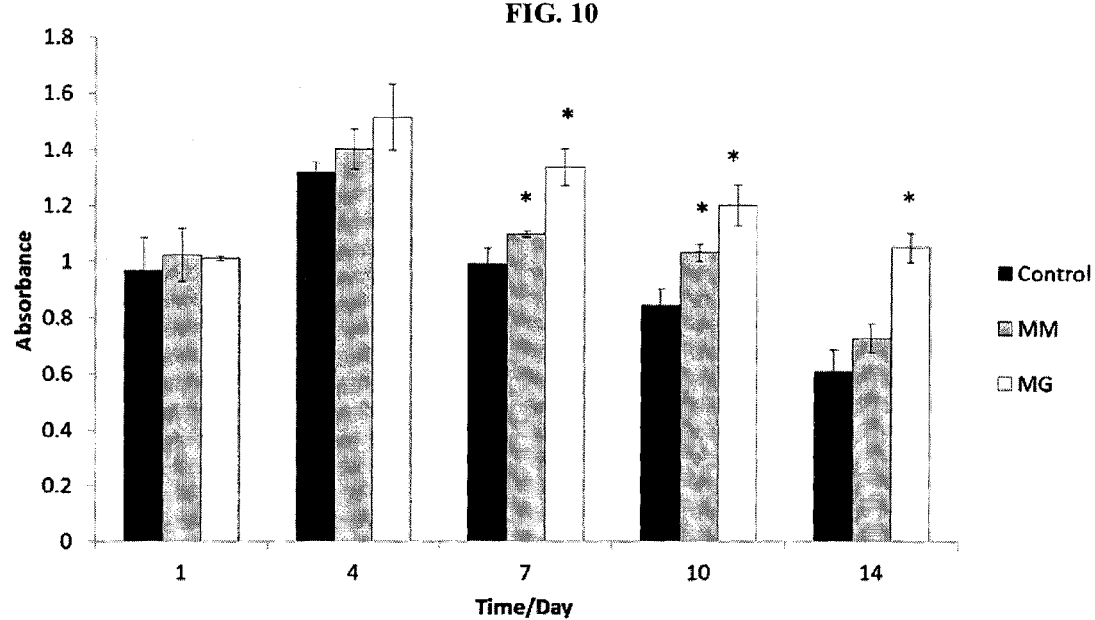
FIG. 10 is a graph showing cell proliferation profile of cells in control, MM and MG constructs using WST-1 assay.

Cell viability is an important indicator of the compatibility of the platform with the cells. As illustrated in FIG. 10, WST-1 assay of the various construct groups showed a significant increase in absorbance from day 1 to day 4 but a gradual decrease in the subsequent days. This may be due to a decrease in the cell proliferation rate from the spatial constraint in the hydrogel.

When the cell spheroid fully occupies the space in the cavity, the proliferation rate decreases since there is no more room for further cell expansion. In all time points other than day 1, cells in the MG group had a much higher absorbance than the control group and MM group.

For qualitative analysis, live/dead staining was carried out on day 4, 7 and 14, as shown in FIG. 11. Given the fluorescent properties of microspheres after crosslinking, the microspheres could be easily identified in red and could be clearly observed in the control group. Most cells in the control were stained green but no HepG2 cell spheroids were observed at all the time points tested. On the other hand, viable HepG2 cells aggregates were observed on day 4 in both MM and MG and these aggregates developed into spheroids on day 14. The spheroids were approximately 100±20 μm in size, which were similar in size to the microspheres used.

Example 2.13: Liver-Specific Functions of Cell-Laden Microspheres Hydrogel Composite To investigate the efficacy of spheroid generation with a focus on this novel biomaterial-based cell-delivery platform, human hepatocellular carcinoma cell line, HepG2, is conveniently adopted as a model cell as it fulfils many of the hepatocyte characteristics like albumin secretion and cytochrome P450 (CYP1A1) activity and they are examined as representing hepato-functional parameters in this study. Urea synthesis, being another important feature of hepatocytes, is believed to be deficient in this cell line, although from a number of studies, trace amount of urea production and variation had been detected; in this study it was not tested.

Albumin and CYP1A1 are two important markers of liver specific functions and were assessed on the gene expression and protein levels. In FIG. 12, albumin expression levels in MM and MG were higher than the control group at all time points and all groups had the highest albumin expression level on day 14. The gene expression levels of CYP1A1 on day 4 was 0.15 and 0.13 in the MM and MG groups respectively, and were approximately 5-fold higher compared to the control on the same day. Although CYP1A1 level showed a decreasing trend over the following days, in general, the expression level of the MM and MG groups were higher than the control at most time points.

On the protein level, albumin secretion was evaluated. The values obtained from each construct were normalized to the control sample on day 1 in FIG. 13. There was an increasing trend in albumin secretion from day 1 to 7 followed by a slight decrease from day 7 to 14. Similar to those observed in gene expression, both MM and MG samples had a higher albumin secretion than the control at all the time points.

Example 2.14: In Vivo Nude Mice Subcutaneous Implantation

To investigate spheroid formation capability in the in vivo environment, the constructs were implanted subcutaneously into nude mice on day 1. After 13 days, the samples were retrieved for histological evaluations by H & E and DAPI stainings. The H & E staining in FIG. 14 showed cavities within the construct and that there were cells adjacent to the cavities.

Furthermore, DAPI staining showed distinct cell aggregates within MM and MG constructs (highlighted with arrows) but these aggregates were absent in the control groups. In addition, genipin crosslinked microspheres in the control group did not degrade as shown in the positive red fluorescence in FIG. 14.

Example 2.15: Discussion

Generation of hepatocellular spheroids to preserve its phenotypic properties is one of the major focuses in liver tissue engineering in recent years. Many approaches have been developed but it often requires sophisticated and high precision equipment to facilitate well-defined size spheroids. This inevitably increases the cost of fabrication and makes scaling up challenging. In view of this issue, we have developed a simple set-up that is able to initiate HepG2 model cell spheroids generation within alginate hydrogel bulk with the aid of a genipin crosslinked gelatin microcarrier and MMP-9.

In this study, genipin crosslinked microspheres are dual functioning as they serve as transient cell carriers and also templates for cavity creation. Since typical gelatin microspheres dissolve readily at a physiological temperature of 37° C., genipin, a natural crosslinker is chosen to crosslink the microspheres to ensure maintenance of the microspheres' structural integrity during cell delivery.

It has been determined that a 0.25 wt % concentration of genipin solution would give rise to the desired crosslinking degree after 16 h of incubation. At this crosslinking degree, stability of the microspheres at 37° C. is achieved and at the same time they could be completely degraded via the introduction of MMP-9.

In the plain hydrogel cell encapsulation model, strict confinement imposed by the hydrogel limits aggregate formation in most cases, or results in the development of irregular aggregate structures that cannot be consistently replicated. The results presented here have highlighted the importance of cavities in generating HepG2 spheroids.

A control group was set up where microspheres remained intact throughout the culture period. Although cells remained viable, no spheroid was formed at any of the observed time points. Cells were able to proliferate within the system but the presence of spheres poses spatial constraint and therefore prohibits spheroid formation. On the other hand, the cell carriers were degraded by MMP-9 in MM and MG samples. MMP-9 was added in the media in the MM group while MMP-9 was introduce via the alginate bulk in MG group in order to maintain the advantage of injectability in the system. The cavities created not only bring space for better cell proliferation and spheroid generation; in addition, they mark the boundary for spheroid expansion.

As cell proliferation takes place, the spheroids generated expand in size within the cavities, having an outward expansion force on the surrounding gel bulk. When this outward force is ultimately balanced by the mechanical force from the gel, equilibrium is reached and the spheroid size can no longer expand. Since the cavity size was determined by the microspheres' size and the selected spheres' size did not exceed 200 µm, the size of spheroids generated were within diffusion limits and therefore no necrotic core was observed in them. The liver-specific functionalities of the generated cell spheroids were assessed on transcriptional and protein level. The higher albumin and CYP1A1 gene expressions together with higher albumin secretion levels in MM and MG compared to the control demonstrated better liver-specific function performance in the spheroids formed.

To investigate the feasibility of spheroid formation within this system in an in vivo environment, day 1 constructs from all groups were subcutaneously implanted into nude mice. All samples were retrieved on day 14 for analysis and successful spheroid formation was confirmed as illustrated in FIG. 14.

The DAPI staining highlighted that cell spheroids were only observed in MM and MG samples whereas a uniform single cell distribution of possibly fibroblasts were seen in the control. As mentioned in the results, gelatin microspheres possessed red fluorescent properties after crosslinking with genipin; these microspheres remained detectable in the control samples after 13 days of implantation.

Accordingly, the optimized crosslinking degrees in the gelatin microspheres achieved ideal properties of a cell carrier where it is able to deliver cells to target site yet it can easily degrade so as not to interfere with further cell expansion. The importance of cavities is highlighted in this study where they are essential for creating space for spheroid formation and also regulation of spheroid size. The positive heptocellular traits found in these MM and MG constructs suggested that spheroids generated in this platform could enhance and preserve the liver cell phenotype. Based on the similar outcome obtained between MM and MG groups; it also proved that the introduction of MMP-9, by mixing it with alginate precursor solution, does not affect cell viability and subsequent cell functionalities. Hence, this system is injectable and has minimal invasiveness.

In addition, many studies have proved better functionality of liver cells spheroid by co-culturing them with endothelial cells, fibroblasts, epithelial cells and hepatic stellate cells. The platform established in this study is customizable as it can also be easily modified to set up a co-culture system by simply adding a second cell type into the alginate precursor solution. The hepatocellular spheroids would reside in the cavities while the second cell type would be in the gel phase of the construct.

In conclusion, a platform which does not require sophisticated equipment yet is able to generate hepatocellular spheroids with controllable size and shape has been set up. Formation of model hepatocellular aggregates in a hydrogel scaffold using degradable genipin crosslinked gelatin microspheres as cell carriers has been demonstrated. The genipin crosslinked gelatin microspheres employed in this study were dual-functioning as they were both cell carriers and porogens for cavity creation within the alginate bulk. HepG was used as a model cell to demonstrate the feasibility of hepatocellular spheroid formation and maintenance of liver specific functionalities in this system. Upon this success, the technology could be adapted for use of hepatocytes or progenitors. It is believed that by this translation, it may ultimately benefit clinical applications.

Primary hepatocyte is probably the preferred cell for cell therapy in liver regeneration. However, its non-ideal proliferation capacity and rapid loss of phenotype during 2D culture compromises the quality and quantity of the transplanted hepatocytes, resulting in variable success rates of this treatment. Many studies have shown that the formation of 3D hepatocellular spheroids aids in the maintenance of liver-specific functions in hepatocytes.

However, many of the methodologies employed require a sophisticated set-up or specialized equipment which makes it uneconomical to scale up for clinical applications. In this study, dual-functioning genipin crosslinked gelatin microspheres that serve as cell carriers as well as porogens for delivering the model cells and also for creating cavities have been developed. The cells were first seeded onto genipin crosslinked gelatin microspheres for attachment, followed by encapsulation in alginate hydrogel. Collagenase, MMP-9, was introduced either in the culture media or mixed with alginate precursor solution to allow microsphere degradation for creating cavities within the gel bulk. Accordingly, the cells proliferate within the cavities, forming hepatocellular aggregates while the alginate hydrogel serves as a confinement, restricting the size and the shape of the aggregates to the size of the cavities. In addition, the final hepatocellular aggregates could be harvested from the system by removing the alginate hydrogel via citrate treatment. Therefore, this versatile platform not only has the advantage of injectability and simplicity, the cellular aggregates generated are in a controlled size and shape and can be extracted from the system.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of manufacturing hydrogel constructs comprising one or more species of living eukaryotic cells encapsulated therein, the method comprising:
    a) dissolving a hydrogel-forming agent in an aqueous medium to form a solution;
    b) suspending one or more species of living eukaryotic cells in the solution to form a cell suspension;
    c) dispersing the cell suspension into an organic oil to form a microemulsion;
    d) subjecting the microemulsion to conditions that allow the hydrogel-forming agent to form hydrogel microparticles comprising said one or more species of living eukaryotic cells encapsulated and uniformly dispersed therein, wherein the hydrogel-forming agent solidifies to form the hydrogel microparticles;
    e) mixing the cell-laden hydrogel microparticles with a second hydrogel solution;
    f) suspending one or more species of living eukaryotic cells in the mixture of the cell-laden hydrogel microparticles and the second hydrogel solution;
    g) subjecting the mixture from step f) to conditions that allow the second hydrogel to form at least one hydrogel comprising the cell-laden hydrogel microparticles encapsulated therein; and
    h) degrading the hydrogel-forming agent of the encapsulated cell-laden hydrogel microparticles from step g) by melting by means of heat treatment at a temperature in the range from 20° C. to 37° C.,
    wherein the hydrogel-forming agent comprises a physically cross-linkable polymer selected from the group consisting of gelatin, alginate, pectin, furcellaran, carageenan, chitosan, derivatives thereof, copolymers thereof, and mixtures thereof.

2. The method according to claim 1, wherein the hydrogel-forming agent comprises or consists essentially of gelatin.

3. The method according to claim 1, wherein the amount of hydrogel-forming agent in the solution is about 5% (w/v).

4. The method according to claim 1, wherein the living eukaryotic cells of either one or both of step b) and step f) are mammalian cells.

5. The method according to claim 1, wherein the eukaryotic cells are non-anchorage dependent cells selected from the group consisting of chondrocytes, embryonic stem cells, adult stem cells, endodermal lineage cells, and carcinoma cells used for regenerative medicine.

6. The method according to claim 1, wherein the living eukaryotic cells of either one or both of step b) and step f) comprise or consist essentially of chondrocytes.

7. The method according to claim 1, wherein the eukaryotic cells are anchorage dependent cells selected from the group consisting of osteogenic cells, fibroblasts, epidermal cells, adipocytes, neural cells, endothelial cells, epithelial cells, keratinocytes, hepatocytes, myocytes, cells from joint ligaments, and cells from the nucleus pulposus.

8. The method according to claim 1, wherein the organic oil is selected from the group consisting of soya oil, corn oil, sunflower oil, rapeseed oil, cotton seed oil, peanut oil, olive oil, sesame seed oil, rice germ oil, fish oil, whale oil, palm oil, coconut oil, hemp oil, canola oil, wheat germ oil, safflower oil, linseed oil, tung oil, castor oil, and mixtures thereof.

9. The method according to claim 1, wherein dissolving the hydrogel-forming agent in the aqueous medium in step a) is carried out at a temperature of about 37° C.

10. The method according to claim 1, wherein subjecting the microemulsion to conditions that allow the hydrogel-forming agent to form hydrogel microparticles comprises cooling the microemulsion at a temperature in the range from about 0° C. to about 10° C.

11. The method according to claim 1, further comprising extracting the organic oil after the hydrogel microparticles are formed; and at least one centrifugation and at least one washing step after extracting the organic oil.

12. The method according to claim 1, wherein the second hydrogel is alginate, agarose, chitosan, dextran, starch or gellan gum.

13. The method according to claim 1, further comprising degrading the second hydrogel to obtain a scaffold-free cellular aggregate, wherein the second hydrogel is degraded with sodium citrate.

* * * * *

SEQUENCE LISTING

```
<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Forward Primer Sequence for Collagen Type 1

<400> SEQUENCE: 1
```

```
cctgcgtgta ccccactca                                                    19

<210> SEQ ID NO 2
<211> LENGTH: 22
<212> TYPE: DNA
<213> ORGANISM: Artificial Sequence
<220> FEATURE:
<223> OTHER INFORMATION: Reverse Primer Sequence for Collagen Type 1

<400> SEQUENCE: 2
accagacatg cctcttgtcc tt                                                22

<210> SEQ ID NO 3
<211> LENGTH: 24
<212> TYPE: DNA
<213> ORGANISM: Artificial Sequence
<220> FEATURE:
<223> OTHER INFORMATION: Forward Primer Sequence for Collagen Type 2

<400> SEQUENCE: 3
gctatggaga tgacaacctg gctc                                              24

<210> SEQ ID NO 4
<211> LENGTH: 24
<212> TYPE: DNA
<213> ORGANISM: Artificial Sequence
<220> FEATURE:
<223> OTHER INFORMATION: Reverse Primer Sequence for Collagen Type 2

<400> SEQUENCE: 4
cacttaccgg tgtgtttcgt gcag                                              24

<210> SEQ ID NO 5
<211> LENGTH: 22
<212> TYPE: DNA
<213> ORGANISM: Artificial Sequence
<220> FEATURE:
<223> OTHER INFORMATION: Forward Primer Sequence for Aggrecan

<400> SEQUENCE: 5
cgaggagcag gagtttgtca ac                                                22

<210> SEQ ID NO 6
<211> LENGTH: 22
<212> TYPE: DNA
<213> ORGANISM: Artificial Sequence
<220> FEATURE:
<223> OTHER INFORMATION: Reverse Primer Sequence for Aggrecan

<400> SEQUENCE: 6
atcatcacca cgcagtcctc tc                                                22

<210> SEQ ID NO 7
<211> LENGTH: 20
<212> TYPE: DNA
<213> ORGANISM: Artificial Sequence
<220> FEATURE:
<223> OTHER INFORMATION: Forward Primer Sequence for Rhoa

<400> SEQUENCE: 7
agctgggcag gaagattatg                                                   20

<210> SEQ ID NO 8
<211> LENGTH: 20
<212> TYPE: DNA
<213> ORGANISM: Artificial Sequence
```

<220> FEATURE:
<223> OTHER INFORMATION: Reverse Primer Sequence for Rhoa

<400> SEQUENCE: 8
tgtgctcatc attccgaaga                                               20

<210> SEQ ID NO 9
<211> LENGTH: 24
<212> TYPE: DNA
<213> ORGANISM: Artificial Sequence
<220> FEATURE:
<223> OTHER INFORMATION: Forward Primer Sequence for Integrin beta1

<400> SEQUENCE: 9
tgccaaatca tgtggagaat gtat                                          24

<210> SEQ ID NO 10
<211> LENGTH: 22
<212> TYPE: DNA
<213> ORGANISM: Artificial Sequence
<220> FEATURE:
<223> OTHER INFORMATION: Reverse Primer Sequence for Integrin beta1

<400> SEQUENCE: 10
gtctgtggct cccctgatct ta                                            22

<210> SEQ ID NO 11
<211> LENGTH: 18
<212> TYPE: DNA
<213> ORGANISM: Artificial Sequence
<220> FEATURE:
<223> OTHER INFORMATION: Forward Primer Sequence for Sox9

<400> SEQUENCE: 11
gctggcggat cagtaccc                                                 18

<210> SEQ ID NO 12
<211> LENGTH: 18
<212> TYPE: DNA
<213> ORGANISM: Artificial Sequence
<220> FEATURE:
<223> OTHER INFORMATION: Reverse Primer Sequence for Sox9

<400> SEQUENCE: 12
cgcggctggt acttgtaa                                                 18

<210> SEQ ID NO 13
<211> LENGTH: 19
<212> TYPE: DNA
<213> ORGANISM: Artificial Sequence
<220> FEATURE:
<223> OTHER INFORMATION: Forward Primer Sequence for Cartilage
      oligomeric matrix protein (COMP)

<400> SEQUENCE: 13
ggcacattcc acgtgaaca                                                19

<210> SEQ ID NO 14
<211> LENGTH: 20
<212> TYPE: DNA
<213> ORGANISM: Artificial Sequence
<220> FEATURE:
<223> OTHER INFORMATION: Reverse Primer Sequence for Cartilage
      oligomeric matrix protein (COMP)

<400> SEQUENCE: 14

```
ggtttgcctg ccagtatgtc                                                  20

<210> SEQ ID NO 15
<211> LENGTH: 24
<212> TYPE: DNA
<213> ORGANISM: Artificial Sequence
<220> FEATURE:
<223> OTHER INFORMATION: Forward Primer Sequence for TBP1 (Reference
      gene)

<400> SEQUENCE: 15
acagttcagt agttatgagc caga                                             24

<210> SEQ ID NO 16
<211> LENGTH: 20
<212> TYPE: DNA
<213> ORGANISM: Artificial Sequence
<220> FEATURE:
<223> OTHER INFORMATION: Reverse Primer Sequence for TBP1 (Reference
      gene)

<400> SEQUENCE: 16
agatgttctc aaacgcttcg                                                  20

<210> SEQ ID NO 17
<211> LENGTH: 20
<212> TYPE: DNA
<213> ORGANISM: Artificial Sequence
<220> FEATURE:
<223> OTHER INFORMATION: Forward Primer Sequence for hbeta-Actin

<400> SEQUENCE: 17
gtggggcgcc ccaggcacca                                                  20

<210> SEQ ID NO 18
<211> LENGTH: 24
<212> TYPE: DNA
<213> ORGANISM: Artificial Sequence
<220> FEATURE:
<223> OTHER INFORMATION: Reverse Primer Sequence for hbeta-Actin

<400> SEQUENCE: 18
ctccttaatg tcacgcacga tttc                                             24

<210> SEQ ID NO 19
<211> LENGTH: 20
<212> TYPE: DNA
<213> ORGANISM: Artificial Sequence
<220> FEATURE:
<223> OTHER INFORMATION: Forward Primer Sequence for hCYP1A1

<400> SEQUENCE: 19
tctttctctt cctggctatc                                                  20

<210> SEQ ID NO 20
<211> LENGTH: 20
<212> TYPE: DNA
<213> ORGANISM: Artificial Sequence
<220> FEATURE:
<223> OTHER INFORMATION: Reverse Primer Sequence for hCYP1A1

<400> SEQUENCE: 20
ctgtctcttc ccttcactct                                                  20

<210> SEQ ID NO 21
<211> LENGTH: 20
```

```
<212> TYPE: DNA
<213> ORGANISM: Artificial Sequence
<220> FEATURE:
<223> OTHER INFORMATION: Forward Primer Sequence for hALB

<400> SEQUENCE: 21
gtgggcagca aatgttgtaa                                           20

<210> SEQ ID NO 22
<211> LENGTH: 20
<212> TYPE: DNA
<213> ORGANISM: Artificial Sequence
<220> FEATURE:
<223> OTHER INFORMATION: Reverse Primer Sequence for hALB

<400> SEQUENCE: 22
tcatcgactt ccagagctga                                           20
```